United States Patent [19]
Cheng et al.

[11] Patent Number: 6,071,394
[45] Date of Patent: Jun. 6, 2000

[54] CHANNEL-LESS SEPARATION OF BIOPARTICLES ON A BIOELECTRONIC CHIP BY DIELECTROPHORESIS

[75] Inventors: Jing Cheng; Edward L. Sheldon, III; Lei Wu; James P. O'Connell, all of San Diego, Calif.

[73] Assignee: Nanogen, Inc., San Diego, Calif.

[21] Appl. No.: 09/016,596

[22] Filed: Jan. 30, 1998

Related U.S. Application Data

[63] Continuation-in-part of application No. 08/709,358, Sep. 6, 1996.

[51] Int. Cl.⁷ ........................................ G01N 27/26
[52] U.S. Cl. .................. 204/547; 204/643; 435/173.7; 435/173.9
[58] Field of Search ........................... 204/547, 545, 204/600, 643, 403, 409; 435/173.7, 173.9, 817, 306.1, 285.2, 287.2, 288.5; 422/63, 81, 50, 129

[56] References Cited

U.S. PATENT DOCUMENTS

| | | |
|---|---|---|
| 3,346,479 | 10/1967 | Natelson . |
| 3,375,187 | 3/1968 | Buchler . |
| 3,533,933 | 10/1970 | Strauch . |
| 3,539,493 | 11/1970 | Dorman . |
| 3,616,454 | 10/1971 | Levy et al. . |
| 3,640,813 | 2/1972 | Nerenberg . |
| 3,697,405 | 10/1972 | Butter et al. . |
| 3,773,648 | 11/1973 | Van Welzen et al. . |
| 3,791,950 | 2/1974 | Allington . |
| 3,902,986 | 9/1975 | Nees . |
| 3,980,546 | 9/1976 | Caccavo . |
| 4,111,785 | 9/1978 | Roskam . |
| 4,390,403 | 6/1983 | Batchelder ............................. 204/547 |
| 4,441,972 | 4/1984 | Pohl . |
| 4,479,861 | 10/1984 | Hediger . |
| 4,661,451 | 4/1987 | Hansen ................................... 435/174 |

(List continued on next page.)

FOREIGN PATENT DOCUMENTS

| | | |
|---|---|---|
| 0 287 513 | 10/1988 | European Pat. Off. . |
| 0 471 949 | 2/1992 | European Pat. Off. . |
| 4400955 A1 | 6/1995 | Germany . |
| WO 93/05166 | 3/1993 | WIPO . |
| WO 96/07917 | 3/1996 | WIPO . |
| WO 97/08293 | 3/1997 | WIPO . |

OTHER PUBLICATIONS

Fuhr et al., *Positioning and Manipulation of Cells and Microparticles Using Miniaturized Electric Field Traps and Travelling Waves;* Sensors and Materials, vol. 7, No. 2 (1995) 131–146.

"Dielectrophoretic characterization and separation of micro–organisms", Markx et al., *Microbiology* (1994) 140, 585–591.

(List continued on next page.)

*Primary Examiner*—Robert J. Warden, Sr.
*Assistant Examiner*—Andrew Aldag
*Attorney, Agent, or Firm*—Lyon & Lyon LLP

[57] ABSTRACT

The present invention comprises devices and methods for performing channel-less separation of cell particles by dielectrophoresis, DC high voltage-pulsed electronic lysis of separated cells, separation of desired components from crude mixtures such as cell lysates, and/or enzymatic reaction of such lysates, all of which can be conducted on a single bioelectronic chip. A preferred embodiment of the present invention comprises a cartridge (10) including a microfabricated silicon chip (12) on a printed circuit board (14) and a flow cell (16) mounted to the chip (12) to form a flow chamber. The cartridge (10) also includes output pins (22) for electronically connecting the cartridge (10) to an electronic controller. The chip (12) includes a plurality of circular microelectrodes (24) which are preferably coated with a protective permeation layer which prevents direct contact between any electrode and a sample introduced into the flow chamber. The permeation layer also helps to reduce cell adhesion at field minima, and enables immobilization of specific antibodies for specific cell capture. Specific cells from various cell mixtures were separated, lysed, and enzymatically digested on the chip.

25 Claims, 15 Drawing Sheets

U.S. PATENT DOCUMENTS

| | | |
|---|---|---|
| 4,699,706 | 10/1987 | Burd et al. . |
| 4,787,963 | 11/1988 | MacConnell . |
| 4,877,510 | 10/1989 | Chen . |
| 4,908,112 | 3/1990 | Pace . |
| 5,126,022 | 6/1992 | Soane et al. ............... 204/643 |
| 5,139,637 | 8/1992 | MacConnell . |
| 5,151,189 | 9/1992 | Hu et al. . |
| 5,161,165 | 11/1992 | Huynh . |
| 5,209,831 | 5/1993 | MacConnell . |
| 5,217,593 | 6/1993 | MacConnell . |
| 5,269,931 | 12/1993 | Hu et al. . |
| 5,340,449 | 8/1994 | Shukla . |
| 5,344,535 | 9/1994 | Betts et al. ............... 204/547 |
| 5,376,249 | 12/1994 | Afeyan et al. . |
| 5,382,511 | 1/1995 | Stapleton . |
| 5,434,049 | 7/1995 | Okano . |
| 5,451,500 | 9/1995 | Stapleton . |
| 5,569,367 | 10/1996 | Betts et al. . |
| 5,589,047 | 12/1996 | Coster et al. ............... 204/450 |
| 5,605,662 | 2/1997 | Heller et al. ............... 422/68.1 |
| 5,653,859 | 8/1997 | Parton et al. . |
| 5,795,457 | 8/1998 | Pethig et al. ............... 204/547 |
| 5,814,200 | 9/1998 | Pethig et al. ............... 204/547 |
| 5,858,192 | 1/1999 | Becker et al. ............... 204/547 |

OTHER PUBLICATIONS

"Dielectrophoretic Manipulation of Particles", Wang et al., *IEEE Transactions on Industry Applications,* vol. 33, No. 3 (May/Jun. 1997).

"Dielectrophoretic separation of bacteria using a conductivity gradient", Markx et al., *Journal of Biotechnology,* 51 (1996) 175 180.

"Dielectrophoresis: Using Inhomogeneous AC Electrical Fields to Separate and Manipulate Cells", Ronald Pethig, *Critical Reviews in Biotechnology,* 16(4):331–348 (1996).

"Postive and negative dielectrophoretic collection of colloidal particles using interdigitated castellated microelectrodes", Pethig et al., *J. Phys. D: Appl. Phys,* 24 (1992) 881–888.

"The Removal of human leukaemia cells from blood using interdigitated microelectrodes", Becker et al., *J. Phys. D: Appl. Phys.* 27 (1994) 2659–2662.

CHANNEL-LESS SEPARATION OF BIOPARTICLES ON A BIOELECTRONIC CHIP BY DIELECTROPHORESIS

RELATED APPLICATION(S) STATEMENT

This is a continuation-in-part of co-pending application Ser. No. 08/709,358, filed on Sep. 6, 1996, the specification of which is hereby incorporated by reference as if fully set forth herein.

FEDERAL FUNDS STATEMENT

This invention was reduced to practice with government support under contract 95-08-009 awarded to Nanogen, Inc. by the U.S. Department of Commerce under the Advanced Technology Program.

FIELD OF THE INVENTION

This invention relates to devices and methods for performing active, multi-step molecular and biological sample preparation and diagnostic analyses. It relates generally to devices and methods for electronic cell separation, cell lysis, and/or enzymatic reaction; and more specifically, to devices and methods for achieving channel-less separation of cell particles by dielectrophoresis, DC high-voltage-pulsed electronic lysis of separated cells, and/or enzymatic reaction, all of which can be conducted on a single bioelectronic chip (e.g. in an integrated assay system). These manipulations are useful in a variety of applications, including, for example, food and/or water quality monitoring, infectious disease diagnostics, diagnostics of cancers, bone marrow processing (e.g. stem cell separation and analysis) and genetics-based identification of individuals for forensics purposes. In addition, these processes and devices can be used in gene expression studies particularly in which a small number of cells of a specific type are to be separated from a large number of other cells for the purpose of studying the RNA of the specific subpopulation.

BACKGROUND OF THE INVENTION

The basis for many molecular-biological and immuno assays, diagnostic assays and tests, among other things, include the steps of obtaining a cellular sample (e.g., blood, tissue, etc.), separating out the cellular material of interest, disrupting or lysing the cells of interest to release the crude DNA and RNA (for simplicity, a reference to DNA in the following text also refers to RNA where appropriate) all protein, purifying the crude lysate (i.e. removing cellular debris), and performing some enzymatic reaction to analyze the lysate as desired.

Dielectrophoresis has become a popular technique for separating microparticles which are either charged or uncharged in solution. Techniques reported prior to this invention are almost always performed in a glass slide based device having exposed (i.e. naked) interdigitated electrodes plated on the surface of the slide and having a flow chamber with a volume of several hundred microliters. Cells are separated in such devices based on their dielectric properties by choosing separation buffer(s) with appropriate conductivity and an AC signal with a suitable amplitude and frequency. These prior devices have several problems, including the following. A first problem is that both separated and unseparated cells bind nonspecifically to the exposed glass surface of the slide and to the exposed electrode surfaces. A second problem is that the volume of the flow chamber (several hundred microliters) is so large that thermal convection disturbs and pushes off cells initially retained by the electrodes. A third problem is that washing off any undesired cells is not easily accomplished without disturbing the cells that are desirably retained on the electrodes, as the desired cells and electrodes stand in the way of fluidic flow and, hence, block the wash flow containing any undesired cells.

Disrupting or lysing cells releases the crude DNA and RNA material along with other cellular constituents. Electronic cell lysing techniques reported prior to this invention are conventionally performed by applying a series of high voltage DC pulses in a macrodevice, as opposed to a microchip-based device. These conventional electronic lysis techniques have several problems, including the following. A first problem is that the electronic lysis conditions specified by commercial macro-device do not release DNA molecules of high molecular weight (larger than 20 Kb) because the high molecular weight DNA molecules do not fit through the pores created in the cell membrane by the prior lysing methods. A second problem is that some nucleic acids originally released in the lysis chamber are lost due to their non-specific binding to the surface of the lysis chamber. A third problem is that the conventional electronic lysis macrodevice works as a stand alone unit such that both dielectrophoretic cell separation and electronic lysis cannot be performed on the same module.

The crude lysate is then purified (i.e., undesired cellular debris is washed off or separated), and then the purified lysate is subjected to enzymatic reaction(s) to prepare the lysate for hybridization, detection, and analysis. Such reactions may include, for example, denaturing, cleaving, or amplifying the lysate. Only after these sample preparation and DNA processing steps, the actual hybridization reaction is performed, and, finally, detection and data reduction convert the hybridization event into an analytical result. These conventional preparation and processing techniques have several problems, including the following. A first problem is that the steps of sample preparation and processing are typically performed separately and apart from the other main steps of hybridization, detection and analysis. In addition, most of these techniques involve carrying out numerous operations (e.g., pipetting, centrifugations, electrophoresis) on a large number of samples. They are often complex and time consuming, and generally require a high degree of skill. Many a technique is limited in its application by a lack of sensitivity, specificity, or reproducibility. For example, these problems have limited many diagnostic applications of nucleic acid hybridization analysis.

Attempts have been made to use dielectrophoresis to separate and identify cells. For example, U.S. Pat. No. 4,326,934 to Herbert discloses a method and apparatus for cell classification by continuous dielectrophoresis. Cells were separated by making use of both the positive and negative dielectrophoretic movement of cell particles. Separated cells were allowed to be characterized and/or classified by viewing the characteristic deflection distance of cells moving through the two electrodes.

Also, U.S. Pat. No. 5,344,535 to Walter et al. discloses a method and apparatus for the characterization of microorganisms and other particles by dielectrophoresis. Cells were characterized by matching their signature dielectrophoretic collection rates.

And U.S. Pat. No. 5,569,367 to Walter et al. discloses a method and apparatus for separating a mixture using a pair of interdigitated electrodes. The apparatus used two energized interdigitated electrodes that obstruct straight through flow of cells and further separate different types of cells into fractions by applying a nonuniform alternating field. The electrode structure is comprised of interleaved grid-like structures aligned to obstruct flow through the structure.

In addition, attempts have been made to combine certain processing steps or substeps together. For example, various microrobotic systems have been proposed for preparing arrays of DNA probes on a support material. For example, Beattie et al., in *The 1992 San Diego Conference: Genetic Recognition*, November, 1992, used a microrobotic system to deposit micro-droplets containing specific DNA sequences into individual microfabricated sample wells on a glass substrate. Various attempts have been made to describe integrated systems formed on a single chip or substrate, wherein multiple steps of an overall sample preparation and diagnostic system would be included. For example, A. Manz et al., in "Miniaturized Total Chemical Analysis System: A Novel Concept For Chemical Sensing", *Sensors And Actuators*, B1 (1990), pp. 244–248, describe a 'total chemical analysis system' (TAS) which comprises a modular construction of a miniaturized TAS. Sampling, sample transport, any necessary chemical reactions, chromatographic separations as well as detection were to be automatically carried out. Yet another proposed integrated system is Stapleton, U.S. Pat. No. 5,451,500, which describes a system for automated detection of target nucleic acid sequences in which multiple biological samples are individually incorporated into matrices containing carriers in a two-dimensional format. Different types of carriers are described for different kinds of diagnostic tests or test panels.

Various multiple electrode systems are disclosed which purport to perform multiple aspects of biological sample preparation or analysis. Pace, U.S. Pat. No. 4,908,112, entitled "Silicon Semiconductor Wafer for Analyzing Micronic Biological Samples" describes an analytical separation device in which a capillary-sized conduit is formed by a channel in a semiconductor device, wherein electrodes are positioned in the channel to activate motion of liquids through the conduit. Pace states that the dimension transverse to the conduit is less than 100 $\mu$m. Pace also states that all functions of an analytical instrument may be integrated within a single silicon wafer: sample injection, reagent introduction, purification, detection, signal conditioning circuitry, logic and on-board intelligence. Soane et al., in U.S. Pat. No. 5,126,022, entitled "Method and Device for Moving Molecules by the Application of a Plurality of Electrical Fields", describes a system by which materials are moved through trenches by application of electric potentials to electrodes in which selected components may be guided to various trenches filled with antigen-antibodies reactive with given charged particles being moved in the medium or moved into contact with complementary components, dyes, fluorescent tags, radiolabels, enzyme-specific tags or other types of chemicals for any number of purposes such as various transformations which are either physical or chemical in nature. It is said that bacterial or mammalian cells, or viruses may be sorted by complicated trench networks by application of potentials to electrodes where movement through the trench network of the cells or viruses by application of the fields is based upon the size, charge or shape of the particular material being moved. Clark, U.S. Pat. No. 5,194,133, entitled "Sensor Devices", discloses a sensor device for the analysis of a sample fluid which includes a substrate in a surface of which is formed an elongate micro-machined channel containing a material, such as starch, agarose, alginate, carrageenan or polyacrylamide polymer gel, for causing separation of the sample fluid as the fluid passes along the channel. The biological material may comprise, for example, a binding protein, an antibody, a lectin, an enzyme, a sequence of enzymes, or a lipid.

Various devices for eluting DNA from various surfaces are known. Shukla U.S. Pat. No. 5,340,449, entitled "Apparatus for Electroelution" describes a system and method for the elution of macromolecules such as proteins, DNA and RNA from solid phase matrix materials such as polyacrylamide, agarose and membranes such as PVDF in an electric field. Materials are eluted from the solid phase into a volume defined in part by molecular weight cut-off membranes. Okano, U.S. Pat. No. 5,434,049, entitled "Separation of Polynucleotides Using Supports Having a Plurality of Electrode-Containing Cells" discloses a method for detecting a plurality of target polynucleotides in a sample, the method including the step of applying a potential to individual chambers so as to serve as electrodes to elute captured target polynucleotides, the eluted material is then available for collection.

Generally, the prior art processes have been extremely labor and time intensive. Multiple steps requiring human intervention either during the process or between processes are suboptimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, numerous attempts have been made to provide effective techniques to conduct sample separation and preparation reactions. However, for the reasons stated above, these techniques are limited and lacking. These various approaches are not easily combined to form a system which can carry out a complete DNA diagnostic assay. Despite the long-recognized need for such a system, no satisfactory solution has been proposed previously.

There is a continuing need for methods and devices which lead to improved dielectrophoretic separation of biological cells as well as improved biological stability of the separated cells. There is also a continuing need for methods and devices which improve cell preparation and analysis, and which are capable of integrating cell separation, preparation, and analysis in a single system.

SUMMARY OF THE INVENTION

This invention broadly relates to devices and methods for performing electronic molecular biological sample separation, lysis, and diagnostic analyses. It relates, more specifically, to devices and methods for achieving channel-less separation of cell particles by dielectrophoresis, DC high voltage-pulsed electronic lysis of separated cells, sample purification (i.e., separation of desired components from crude mixtures such as cell lysates), and/or enzymatic reaction(s), all of which can be conducted on a single bioelectronic chip utilizing the differential mobility and/or differential affinity for various materials in the sample.

In one aspect of this invention, a device comprises a microfabricated silicon chip with a plurality of coated electrodes. The electrodes are preferably coated with a protective layer which prevents direct contact between any electrode and a sample. A covered flow cell is attached to the chip to form a sealed chamber having an in-port and an out-port which may be further attached to plastic tubing to enable input and output of materials through the in-port and out-port respectively.

One exemplary method of using such a device includes preparation of a cell sample for introduction (e.g., suspension in a cell separation buffer) and subsequent dielectrophoresis; introduction of the sample into the flow cell (e.g., via pumping); subjecting the sample to an electric field to dielectrophoretically separate the desired cells from the sample; washing the undesired cells away by pumping solution through the flow cell; and subjecting the remaining (desired) cells to at least one series of electronic pulses to lyse the cells; and/or subjecting the lysate to enzymatic reaction(s) as desired.

Therefore, a primary object of the present invention is to provide devices and methods for conducting cell separation, lysis and/or enzymatic reaction.

An additional object of the present invention is to provide devices and methods for conducting cell separation, lysis, and/or enzymatic reaction(s) on a single chip so that mechanical manipulation such as pipetting and centrifugation can be omitted.

A further object of the present invention is to provide devices and methods for providing a combination of electrode addressing, a buffer, and the use of a permeation layer to accomplish uniform separation of desired cells.

Still a further object of the present invention is to provide devices and methods for providing uniform separation of desired cells with minimized non-specific adhesion of cells to the flow chamber and/or electrodes through the use of a permeation layer.

Yet a further object of the present invention is to provide devices and methods where washing off undesired cells is easily accomplished through washing without channels in the flow chamber.

Another object of the present invention is to lyse the desired cells retained on the electrodes by applying at least one series of high-voltage DC pulses on the electrodes in a highly localized and controlled manner so that both DNA and RNA or protein are released from the cells with their integrity intact.

Still another object of the present invention is to perform in the same flow chamber an enzymatic reaction on the lysate to free the nucleic acids from contaminating proteins, while not causing any loss of DNA or RNA.

Yet another object of the invention is to perform one or more of the above operations, i.e., cell separation, cell lysis, enzymatic deproteinization of DNA/RNA, or nuclease digestion of DNA/RNA, as well as DNA or RNA hybridization, immuno assay, or ligand binding reaction, in a self-contained flow chamber on a single chip.

DETAILED DESCRIPTION OF THE PREFERRED EMBODIMENT

The present invention comprises devices and methods performing channel-less separation of cell particles by dielectrophoresis, DC high voltage-pulsed electronic lysis of separated cells, separation of desired components from crude mixtures such as cell lysates, and/or enzymatic reaction of such lysates, all of which can be conducted on a single bioelectronic chip.

Figure 1:
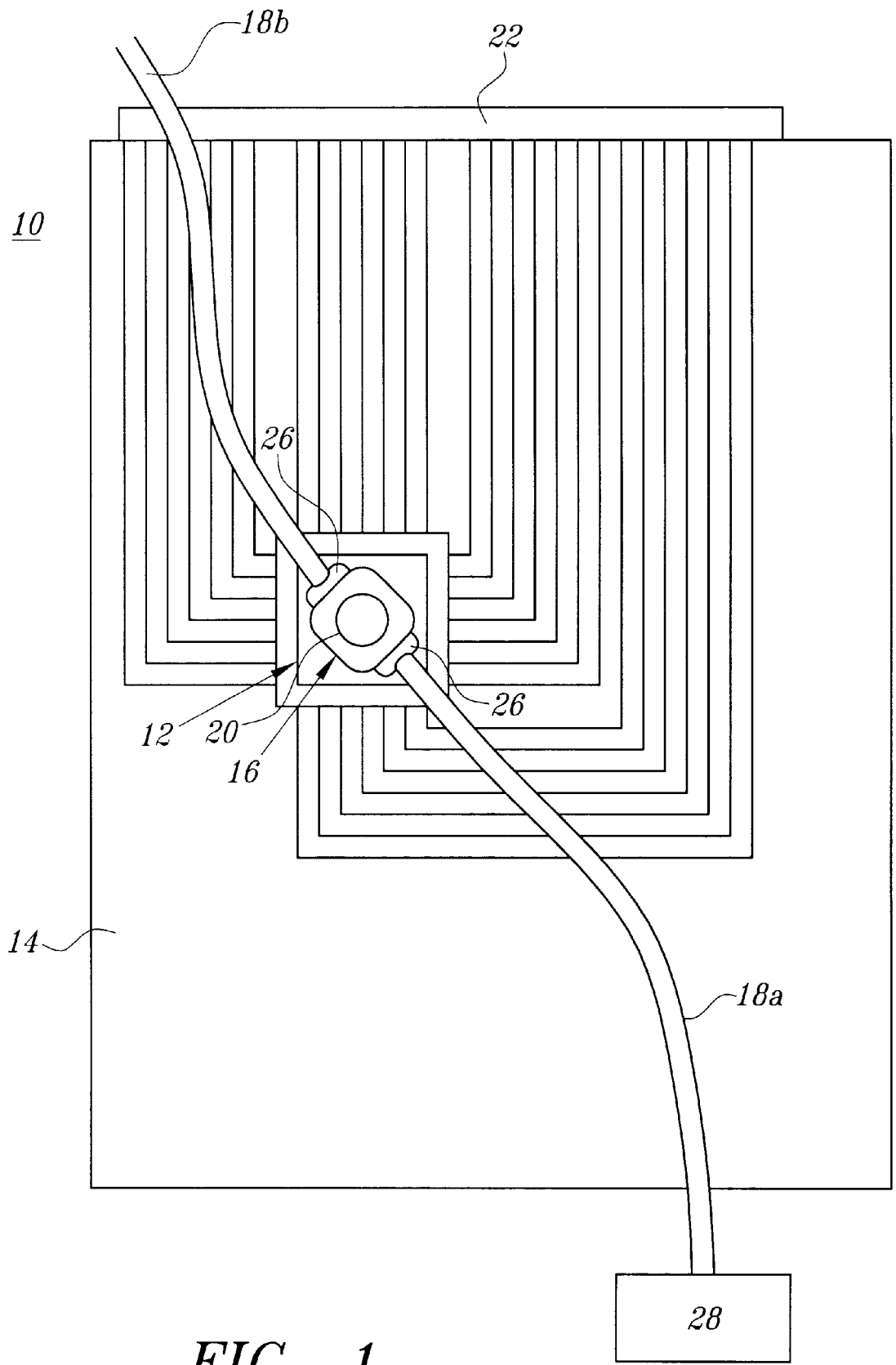
FIG. 1 shows a top view of a device of the present invention bearing a microchip and a flow chamber including fluid tubing and a detection window.

A preferred embodiment of the present invention comprises a cartridge 10, shown in FIG. 1, including a microfabricated silicon chip 12 on a printed circuit board 14, a flow cell 16 mounted to the chip 12 to form a flow chamber including fluid tubing 18a and 18b and a detection window 20. The flow chamber preferably has a volume of about 10 µl. The cartridge 10 also includes output pins 22 for electronically connecting the cartridge 10 to an electronic controller (e.g. instrument or computer) (not shown).

Figure 2:
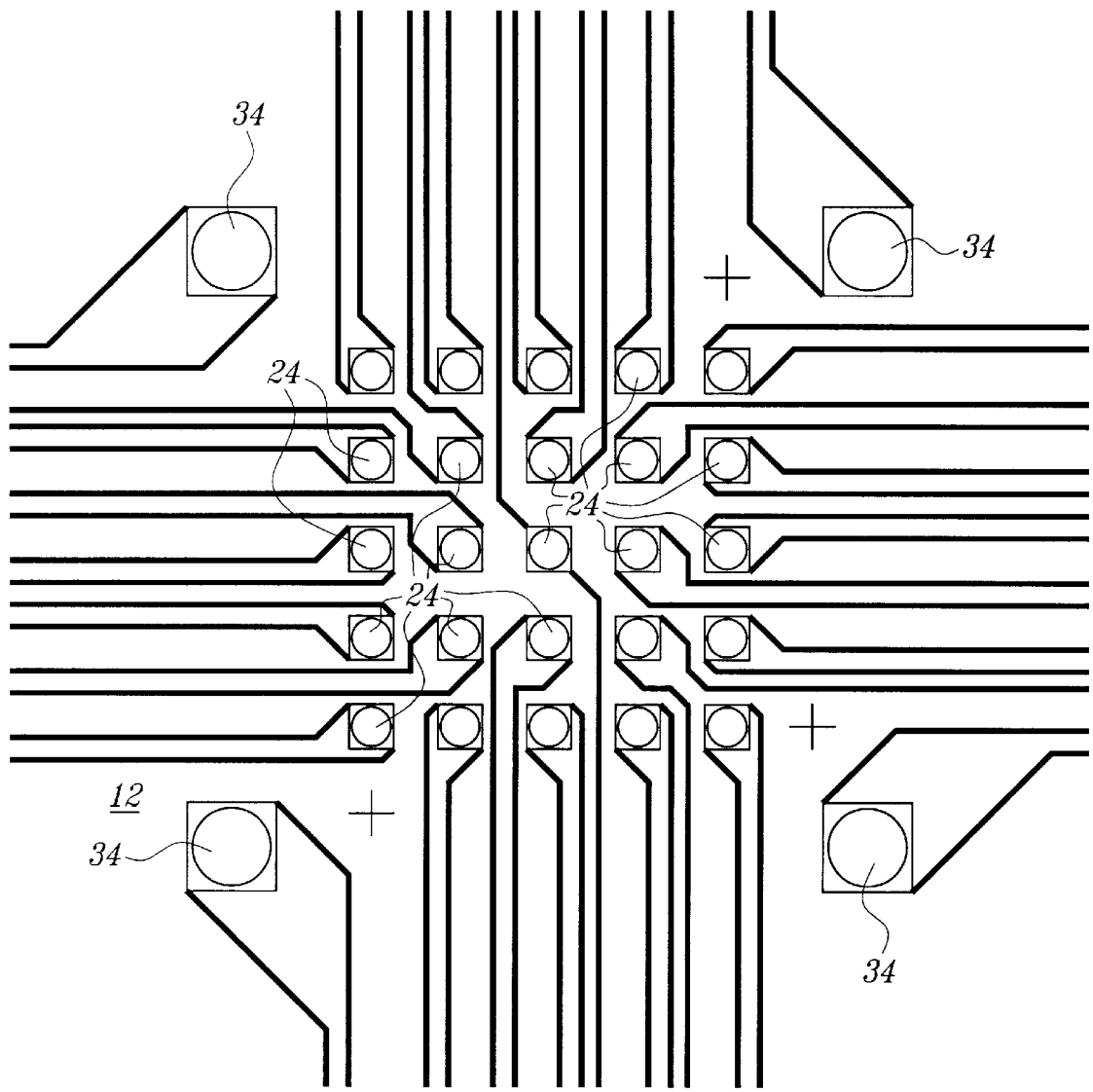
FIG. 2 is the schematic view of a chip coated with a permeation layer showing several circular electrodes and counterelectrodes.
Figure 4A:
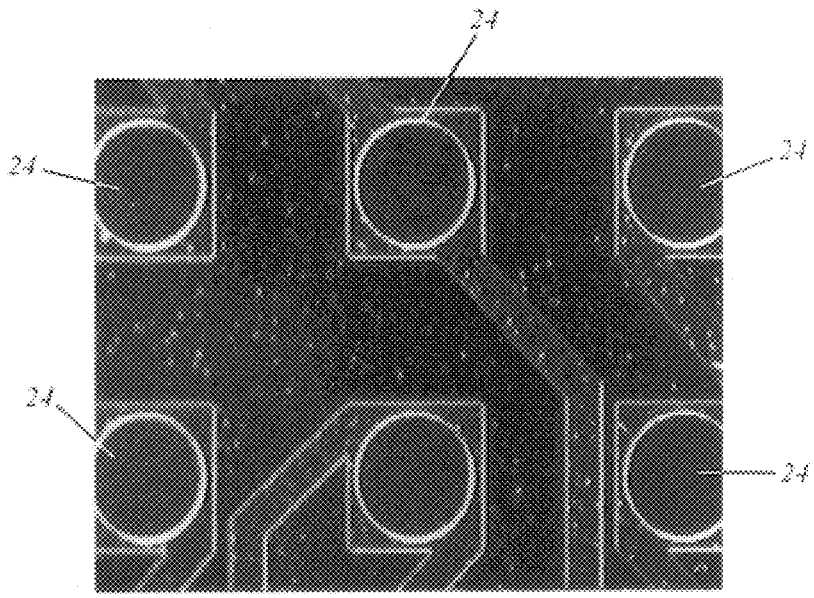
FIG. 4A shows a detailed view of a chip.

The microfabricated chip 12 is shown in FIG. 2 (a detail is shown in FIG. 4A), and, as shown, includes a plurality of circular microelectrodes 24 and counterelectrodes 34. The electrodes 24 are preferably coated with a protective layer which prevents direct contact between any electrode and a sample introduced into the overlying flow cell 16 (explained in more detail below).

In a preferred embodiment, the chip 12 includes four counterelectrodes 34, and five rows each having five platinum microelectrodes 24, and is fabricated using standard semiconductor processing techniques that are well known. It should be noted that the number of electrodes could be more or less than that shown here, and that the present specification uses a five by five arrangement for illustrative purposes only and is not limited to the same. Indeed, a chip with more electrodes could facilitate recovery of a greater number of the targeted cells and, therefore, a higher yield of nucleic acids. The center to center distance between neighboring electrodes 24 is preferably on the order of about 200 µm and the diameter of each electrode 24 is preferably on the order of about 80 µm.

In this embodiment, the chips 12 were prepared by first sputtering a titanium-tungsten (Ti—W) layer onto a thermally-oxidized silicon wafer to a thickness of about 100 nm, and then on the Ti—W layer sputtering a platinum layer to a thickness of about 300 nm. A photolithographically defined wet etch in aqua regia was used to pattern the metallization. Thin films of low stress silicon nitride (1.3 µm) and silicon dioxide (100 nm) were deposited over the surface of the patterned metal by plasmaenhanced chemical vapor deposition. A photolithographically-patterned dry plasma etch was used to etch through the dielectric to the electrode arrays. The chips 12 were each wire-bonded to a printed circuit board 14 (which preferably conforms to the personal computer card standard of the Personal Computer Memory Card International Association).

After bonding the chips 12 to the circuit boards 14, the chips 12 were washed with isopropanol followed by rinses with deionized water. The chips 12 were then blown dry by a stream of nitrogen. The boards 14 bearing the dried chips 12 were then placed vertically in a plasma cleaner boat and cleaned in argon (250 mTorr, 250 W) for five minutes. After the plasma cleaning, a permeation layer was added to each chip 12.

First, a 2.5% bottom permeation layer (BPL) solution of glyoxyl agarose was prepared as follows. Glyoxyl agarose (250 mg) (from Sigma, St. Louis, Mo.) was added to 10 ml of deionized distilled water, mixed, and then boiled for eight minutes. The completely dissolved agarose solution was hot filtered into pre-warmed (65° C.) Eppendorf tubes using a 1.2 µm syringe filter. The filtered agarose solution was equilibrated to 65° C. for five minutes. Next, a top permeation layer (TPL) was prepared as follows. A streptavidin solution (5 mg/ml) was prepared by suspending streptavidin (Boehringer Mannheim, Indianapolis, Ind.) in a solution containing sodium chloride (250 mM) and sodium phosphate (10 mM, pH 7.2). The streptavidin solution was combined with the temperature equilibrated EPL solution to yield 2% agarose and 1 mg/ml streptavidin. The warm BPL solution (50 µl) was placed on each chip and spun in a spincoating apparatus (EC101D, Headway Research, Garland, Tex.) at 2500 rpm for twenty seconds at room temperature. After the BPL was solidified, the warm TPL solution (50 µl) was placed on top of the BPL and spun in the spincoating apparatus at 10,000 rpm for twenty seconds at room temperature. The coated chips were then baked at 37° C. for thirty minutes.

The Schiff base linkage between the glyoxyl agarose and the primary amines of streptavidin was reduced with freshly prepared sodium cyanoborohydride (0.2 M)/sodium borate (0.3 M), pH 9.0, at room temperature for one hour. Remaining aldehyde groups were capped with glycine buffer (0.2 M) in sodium borate (0.3 M), pH 9.0, at room temperature for thirty minutes. The chips were finally rinsed with deionized water for five minutes, air dried for four hours, and then stored at 4° C.

A cartridge 10 of the present invention was completed by selecting a prepared chip 12/printed circuit board 14 and gluing a polycarbonate molded flow cell 16 onto the chip 12 preferably using a UV adhesive (Norland 68, Thorlabs, New Brunswick, N.J.) under a 200 W UV light for forty-five seconds (4 Joules/cm$^2$). Preferably a cover glass slip is glued on top of the flow cell 16 to form a sealed flow chamber using the same procedure. Input and output plastic tubing 18a and 18b, respectively, were added to the in-port and out-port of the flow cell 16 via lure fittings 26 and then glued in place.

The cartridge 10 was then ready for testing. A test was conducted to separate, lyse, and enzymatically react E. coli cells, and a test was conducted to separate cervical carcinoma cells.

The E. coli Test

First a cell culture was prepared using well known techniques. A 296 bp fragment was amplified from the SpaO region of Salmonella enteritidis, then cloned into plasmid pCR 2.1 (3890 bp) using an Invitrogen T/A Cloning Kit (Invitrogen, San Diego, Calif.). Ligation was performed according to kit instructions, and the ligation product was used to transform INVαF' competent E. coli. Transformants were grown up on LB plates supplemented with ampicillin (100 µg/ml), 80 µl of x-gal (20 mg/ml), and 4 µl of isopropylthio-B-D-galactoside (40 mM) for blue/white screening. To screen for clones ten white colonies were picked, and lysed to release DNA for analysis. The DNA was amplified by PCR using SpaO specific primers and the amplicons were examined by gel electrophoresis. One positive clone from the PCR screen was grown up at 37° C. overnight in LB and ampicillin liquid culture (100 µg/ml) with shaking at 225 rpm.

Then a cell culture was prepared using well known techniques. A cell separation buffer comprising 0.05×TBE (4.5 µM Tris, 4.5 µM boric acid, 0.1 µM EDTA, pH 8.2), 250 mM sucrose, pH 8.2, was prepared. The conductivity of the buffer was 114 µS/cm measured by an Accumet pH Meter 50 (Fisher Scientific, Pittsburgh, Pa.). The conductivity under which cell separation was carried out was chosen carefully to ensure that the E. coli cells were subjected to positive dielectrophoresis and all normal human blood cells were subjected to negative dielectrophoresis. The cultured E. coli cell suspension (1 ml) was centrifuged at 325×g for four minutes and the supernatant removed. The cell pellet was washed in the cell separation buffer (1 ml) and pelleted using the same conditions described above. The cells were then re-suspended in cell separation buffer (1 ml). Fresh EDTA-anticoagulated human blood (20 µl) was added to the *E. coli* cell suspension (1 ml), and the cell culture was complete.

The cell culture was introduced into a cartridge 10 of the present invention and dielectrophoresis was conducted to separate out the *E. coli* cells. The cartridge 10 was placed on the stage of a Nikon phase contrast microscope. The lighting was provided by a ring light (Precision MicroOptics, Irvine, Calif.). Image signals were collected by a CCD/RGB color video camera (Sony DXC-151, Mikron Instruments, San Diego, Calif.) through a 10×objective, and were recorded using a Sony VCR and monitored by a Sony television monitor. Fluids were pumped through the tubing 18 and flow cell 16 via a peristaltic pump (Model RP-1, Rainin Instruments, Woburn, Mass.). The signals on electrodes 24 were generated from a function/arbitrary waveform generator (Model HP33120A, Hewlett-Packard, Santa Clara, Calif.) and monitored by an oscilloscope (Model HP54600, Hewlett-Packard).

Prior to actually subjecting the cell culture to dielectrophoresis, computer modeling and dielectric characterization studies were conducted. To facilitate washing off the human blood cells, it was preferred that the *E. coli* cells be subjected to positive dielectrophoresis and all normal human blood cells be subjected to negative dielectrophoresis. Under positive dielectrophoretic force *E. coli* migrates toward the electrode where the positive field maxima occurs. Under negative dielectrophoretic force human blood cells migrate toward the space between the electrodes where the negative field maxima occurs. The frequency at which this occurs was empirically determined based on computer modeling and dielectric characterization studies.

The basic theory of dielectrophoresis, motion of particles with induced polarization under non-uniform electric field, has been extensively studied. See, e.g., R. Pethig, "Dielectrophoresis: Using Inhomogeneous AC Electrical Fields To Separate and Manipulate Cells", *Crit. Rev. Biotech*, 16:331–48 (1996); X. Wang, et al., "A Unified Theory of Dielectrophoresis and Travelling Wave Dielectrophoresis", *J. Phys. D: Appl. Phys.*, 27:1571–74 (1994); G. Fuhr, "Cell Manipulation and Cultivation Under AC Electric Field Influence in Highly Conductive Culture Media", *Biochim. Biophys. Acta* 1158:40–46 (1993); and M. Washizu, "Molecular Dielectrophoresis of Biopolymers", *IEEE Trans. Industry Applicat.* 30:835–43 (1994). The dielectrophoresis phenomenon can be generally described by energy potential $$\psi = -\overline{m} \cdot \overline{E}$$

where $\overline{m}$ is the induced dipole moment of a particle suspended in dielectric medium and $\overline{E}$ is the applied electric field. Therefore, the dielectrophoretic force acting on a particle can be written as a gradient of energy potential.

When the particle has zero net charge and the surrounding medium is isotropic, the average energy potential can be simplified as $$\psi = -(\tfrac{1}{2}) p v E^2$$

where p is the effective polarizability of the suspended particle with volume v. The value and sign of polarizability (p) depends on the permittivity of particle and medium, as well as the frequency of the applied electric field. R. Pethig, "Dielectrophoresis: Using Inhomogeneous AC Electrical Fields To Separate And Manipulate Cells", *Crit. Rev. Biotech.*, 16:331–48 (1996). At steady state, the particle with positive polarizability (p>0) will tend to stay at the high-field region and the particle with negative polarizability (p<0) will stay at the low-field region.

To model the distribution of the electric field around the electrodes 24 of the present invention, the following two assumptions were made: First, within the low frequency range the dimensions of both chip and flow chamber are much smaller than the wavelength of the applied AC field. Second, the sample solution has electroneutrality. Under these two assumptions the electric field can be calculated for a particular addressing configuration in the present experiment set-up by solving Laplace's equation $$\nabla^2 \phi = 0 \text{ and } \overline{E} = -\nabla \phi$$

($\phi$ is electric potential) with boundary conditions of fixed voltage on electrodes and zero normal current on the rest of the surface, $\phi = V_0$ at positive electrodes, $\phi = 0$ at negative electrodes, and $\delta\phi/\delta n = 0$ at the rest of the chip surface and the flow chamber.

The electric field in the sample solution, and, therefore, the energy potential of polarized particles, is numerically calculated by the finite-difference method. See, K. Binns, "The Analytical and Numerical Solution of Electric and Magnetic Fields" (John Wiley & Sons, New York. 1992).

The frequency at which the *E. coli* cells were subject to the positive dielectrophoretic force and blood cells were subject to the negative dielectrophoretic force was empirically determined by subjecting the cell mixture to different conditions. The investigation was conducted by gradually increasing the frequency of the sinusoidal signal (10 volts peak-to-peak) starting from 5 KHz. When the frequency reached 10 KHz, evident separation of *E. coli* cells and the rest of the human blood cells was observed. These electrical parameters were later used for the isolation of the *E. coli* cells.

Figure 3A:
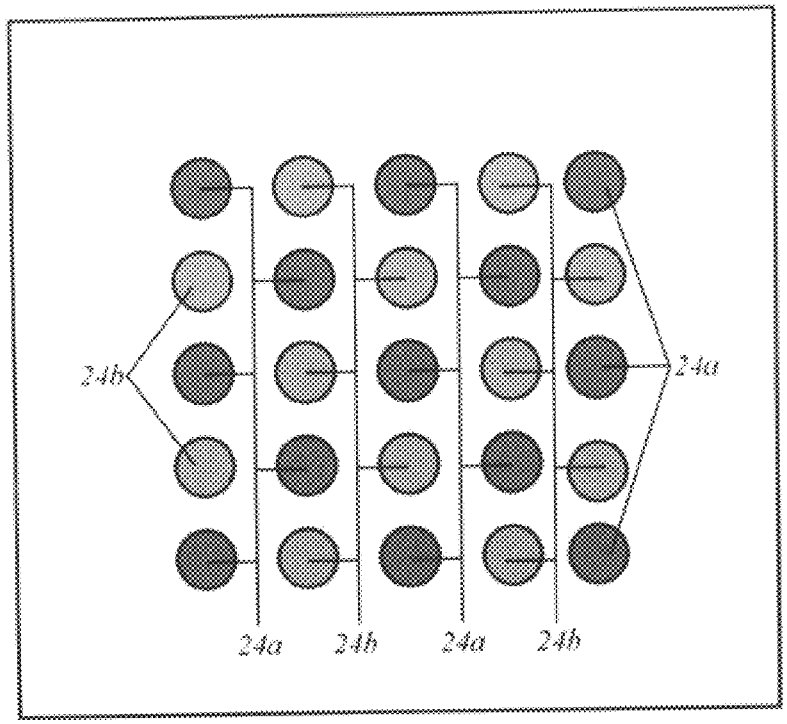
FIG. 3A is a schematic illustration of checkerboard style electronic addressing of a five by five arrangement of circular electrodes where each electrode has opposite biasing as its nearest neighboring electrodes (the use of a five by five arrangement is for illustrative purposes only, the array can have more or less than twenty five electrodes).
Figure 3B:
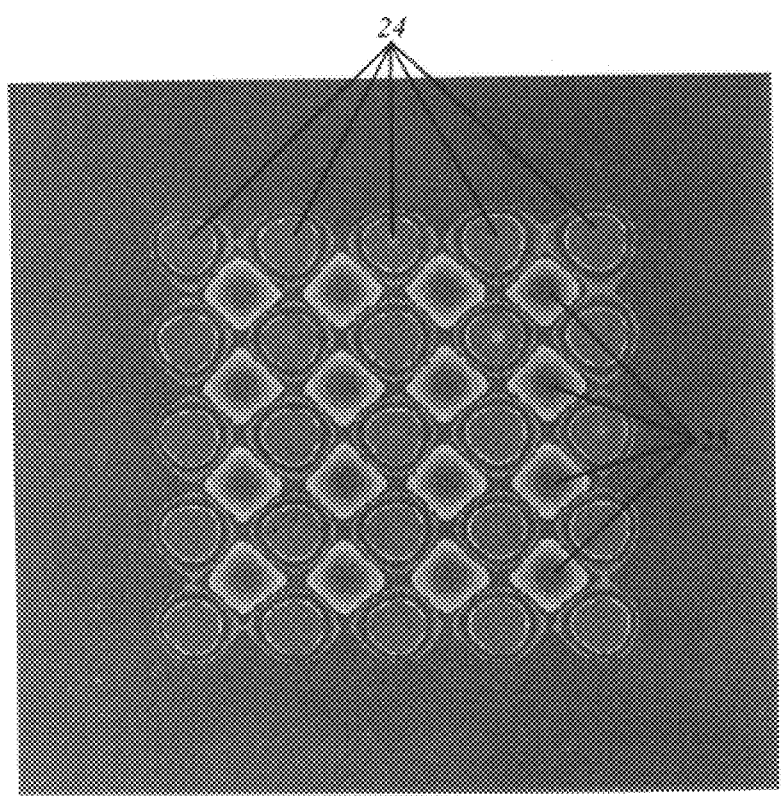
FIG. 3B is a schematic illustration of a computer model of the AC field distribution corresponding to the checkerboard style addressing shown in FIG. 3A where a regular distribution of electric field is obtained with the field maxima at each electrode and field minima in the areas between the electrodes.
Figure 4B:
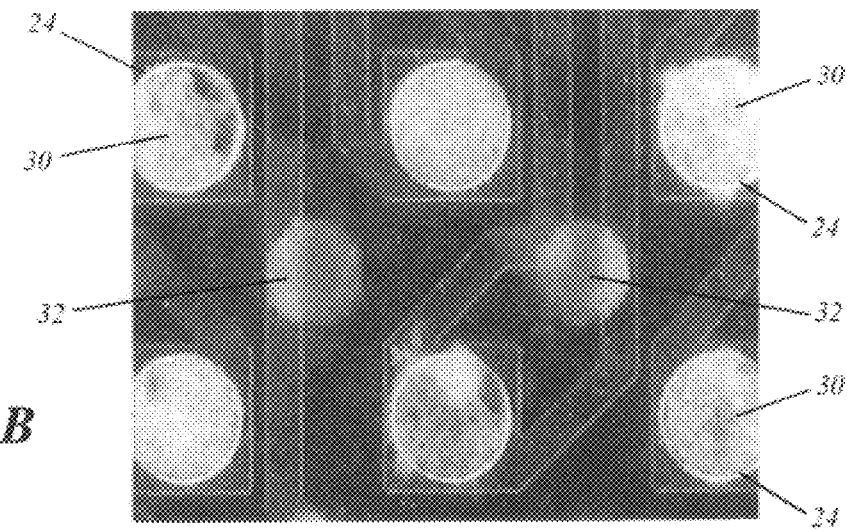
FIG. 4B shows a sample of *E. coli* cells retained on several electrodes of the chip shown in FIG. 4A, and separated from human blood cells (both red and white blood cells) using the checkerboard style electronic addressing shown in FIGS. 3A and 3E.

To perform the dielectrophoretic separation of *E. coli* cells from blood cells in the cell culture, an unused cartridge 10 was employed. The chip 12 of the cartridge 10 was first washed by pumping separation buffer from a sample/buffer reservoir 28 through the tubing 18 and flow cell 16. Next, the cell culture was pumped into the flow cell 16, and the pump was switched off. The entire array of electrodes 24 (i.e. all twenty five electrodes in the five column by five row array) were addressed in a checkerboard bias format providing field maxima at each electrode and field minima in the areas between the electrodes, as shown in FIGS. 3A–3B, by applying a sinusoidal signal of 10 volts peak-to-peak at 10 KHz. As shown in FIG. 4B (and compared to FIG. 4A), the separation of *E. coli* cells 30 (collected at the electrodes 24 at the field maxima) from human blood cells 32 (collected in areas between the electrodes 24 at the field minima) was finished in approximately four minutes. Afterwards, the pump was switched on to start the washing process.

Figure 3C:
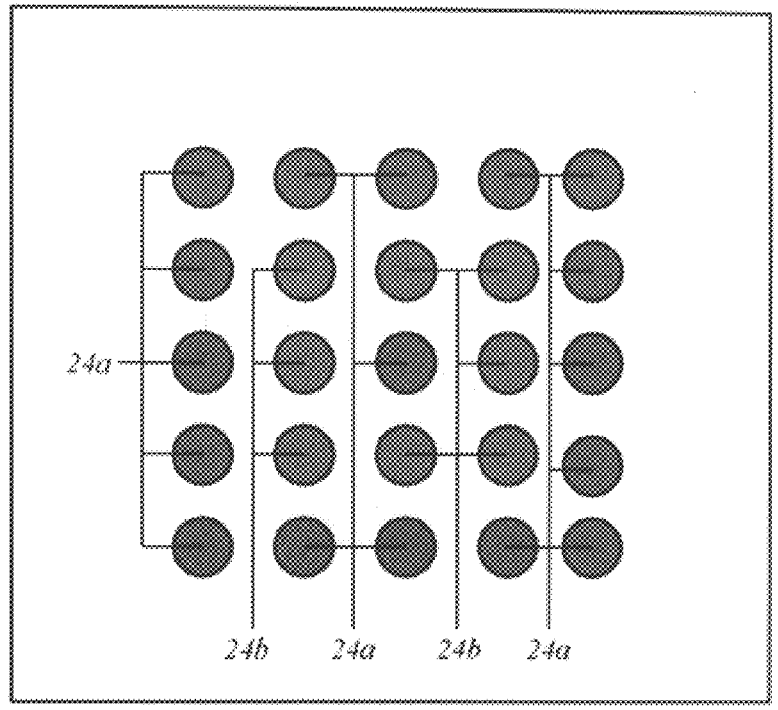
FIG. 3C is a schematic illustration of square wall style electronic addressing of a five by five arrangement of circular electrodes where electrodes on the same square frame have the same biasing which is opposite from those electrodes on the nearest neighboring square frame(s).
Figure 3D:
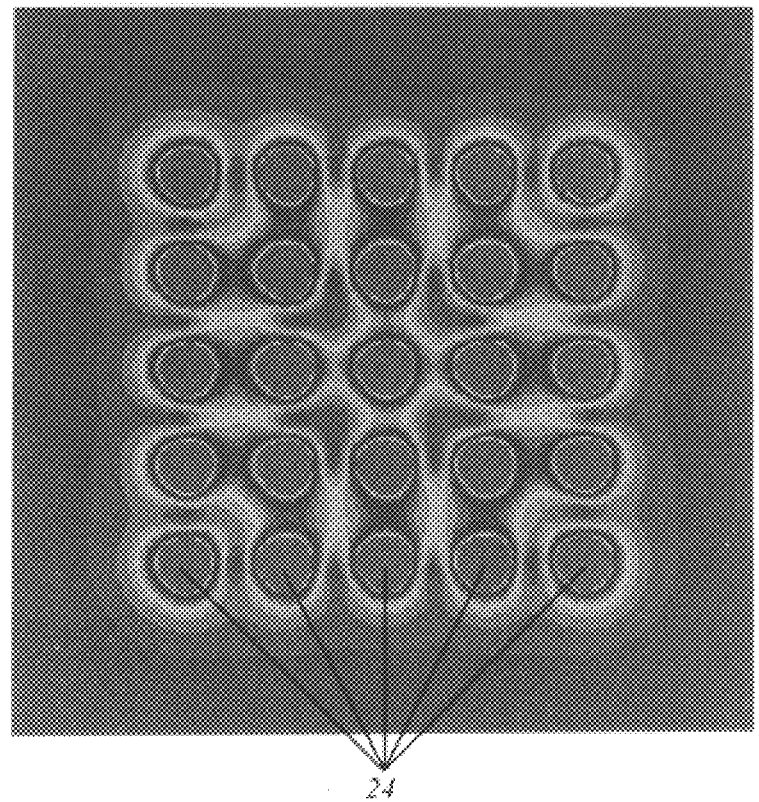
FIG. 3D is a schematic illustration of a computer model of the AC field distribution corresponding to the square wall style addressing shown in FIG. 3C.

The checkerboard biasing format shown in FIG. 3A was used rather than the square wall format shown in FIG. 3C. As is shown in FIG. 3B, the field distribution corresponding to the checkerboard style addressing provides a uniform distribution of the electric field with the field maxima at each electrode and field minima in the areas between the electrodes, whereas, as is shown in FIG. 3D, the square wall style addressing does not provide field minima interspersed between electrodes. Having an arrangement where the field minima are interspersed between electrodes (as shown in FIG. 3B) is preferred because with such an arrangement washing off undesired cells (i.e. those collected in the areas of field minima) is easily accomplished without disturbing the desired cells (i.e. those retained on the electrodes), as the desired cells and electrodes do not stand in the way of fluidic flow and, hence, do not block the washing off flow containing any undesired cells. It should be understood that the checkerboard style addressing could essentially be accomplished by grouping electrodes and having each group of electrodes biased opposite from its nearest neighboring groups of electrodes.

Figure 5:
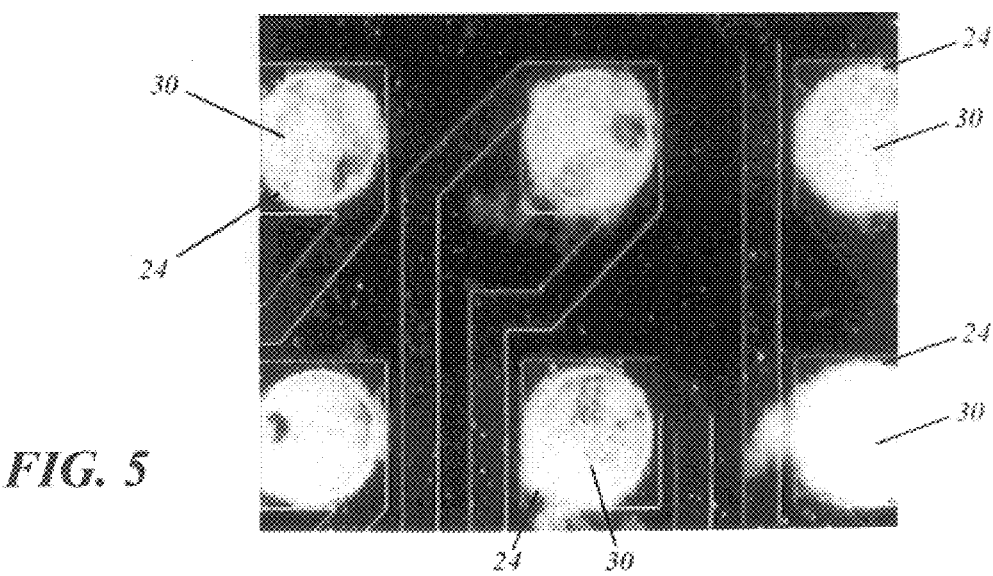
FIG. 5 shows the retained *E. coli* cells of FIG. 4B after the human blood cells are washed away.

When the sample cell culture mixture was nearly drained from the sample/buffer reservoir 28, separation buffer was added to wash the rest of the sample through the flow cell 16 while the AC signal was still on. As is shown in FIG. 5 (as compared to FIG. 4B), the washing process washed away the human blood cells and the E. coli cells 30 were retained. After washing, separation buffer (300 µl) containing proteinase K (490 µg, Boehringer Mannheim, Indianapolis, Ind.) was pumped into the flow chamber 16 to reduce the size of proteins.

Figure 6:
FIG. 6 shows a sample of the nucleic acids released from the *E. coli* cells shown in FIGS. 4B and 5 and concentrated by applying a DC wave.

Electronic lysis was then performed to lyse the retained E. coli cells. To lyse the cells a series of pulses (500 V, 50 µs pulse width) were applied between the four counterelectrodes 34 (shown in FIG. 2) and the twenty-five smaller cell collecting electrodes 24. The pulses were applied in such a way that the polarity of every twenty pulses were alternated between the two groups of electrodes 24 and 34. A total of four hundred pulses were applied for each lysis process. The alternating pulses pushed and pulled material out of the cells. FIG. 6 shows a sample of the nucleic acids 36 released from the E. coli cells and concentrated by applying a DC wave.

The lysate mixture was incubated at 50° C. for twenty minutes to allow digestion of the DNA-contaminating proteins. The lysate was collected by pumping it out of the flow cell 16. The combination of dielectrophoretic separation and electronic lysis were repeated six times and all the lysates were pooled together for analysis.

The pooled lysate was centrifuged at 16000×g for five minutes. Next, the supernatant was recovered and two volumes of chilled ethanol (−20° C.) were added to the solution, mixed and spun at 16000×g for ten minutes. The supernatant was removed and the pellet was dried in air. The pellet was then redissolved in 0.05×TBE buffer (300 µl). A fraction of the redissolved solution (30 µl) was combined with a solution containing RNase (3 µl, 10 mg/ml, Boehringer Mannheim). The combined solution was incubated at 37° C. for thirty minutes.

Figure 7:
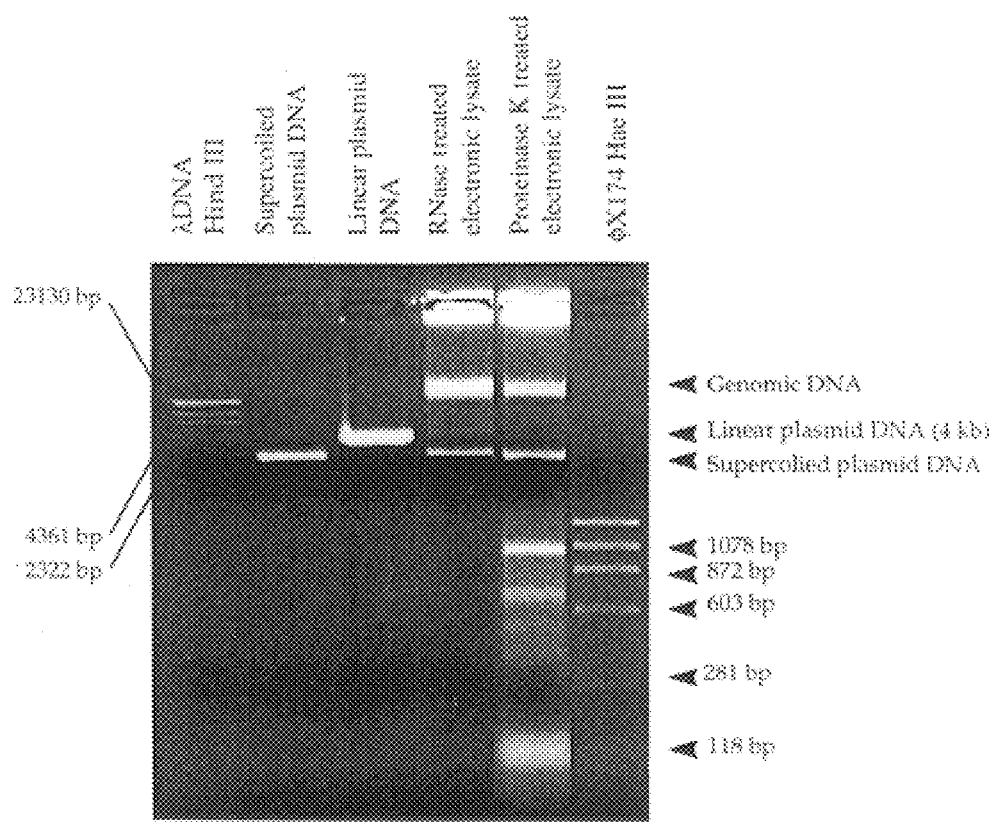
FIG. 7 shows a photographic image taken after analysis by agarose gel electrophoresis of the nucleic acids of FIG. 6 demonstrating that a whole spectrum of nucleic acids ranging from genomic DNA, supercoiled plasmid DNA and RNAs were released from the cells after electronic lysis.

Gel electrophoresis was then conducted to analyze the collected material. A 1.2% agarose gel was prepared by melting 600 mg of agarose in 50 ml of 1×TBE buffer. Ethidium bromide (2.5 µg) was added to the agarose solution before it became solidified. Proteinase K treated lysate samples with or without RNase treatment were loaded onto the gel along with marker DNAs. FIG. 7 shows a photographic image taken after agarose gel electrophoresis of the nucleic acids of FIG. 6 demonstrating that a whole spectrum of nucleic acids ranging from genomic DNA, supercoiled plasmid DNA and RNAs were released from the cells after electronic lysis.

A DNA hybridization assay was then performed. An oligonucleotide capture probe (39-mers) specific for the SpaO region of the plasmid DNA was incorporated with biotin at its 3' end. The capture probe was diluted in 50 mM L-histidine buffer to make a final concentration of 500 nM. The capture probe was immobilized on the test microlocations containing streptavidin with the underlying electrodes 24 positively biased. Electric biasing was performed by maintaining the current on each electrode 24 at 200 nA for one minute. Afterwards, the remaining probe solution was removed and the chip 12 was washed with 50 mM L-histidine buffer. The immobilization of the probes for the controls (ATA5 and GAS probe) was accomplished using the same protocol described above.

To facilitate the hybridization of DNA, a fraction of the proteinase K treated lysate was diluted three and five times respectively in the L-histidine buffer. The diluted lysate samples were boiled in a 100° C. water bath for ten minutes to fragment the DNA (the final size of DNA ranging between 300 bp to 1 Kb) and also to make the DNA single stranded. To verify the presence of the control, the synthesized RCA5 oligonucleotide target (see, F. Becker, et al., "Separation of Human Breast Cancer Cells From Blood By Differential Dielectric Affinity", *Proc. Natl. Acad. Sci. USA* 92:860–64 (1995)) specific for capture probe ATA5 was electronically hybridized to both the immobilized ATA5 probe and the adjacent nonspecific GAS probe in parallel by keeping the current at each electrode at 450 nA for three minutes. When the capture processes were finished fresh L-histidine buffer was loaded to replace the old and to perform the electronic stringency wash. Washing was performed by applying 150 DC pulses to one row at a time, 1 µA per pad with 0.1 seconds on and 0.2 seconds off.

To conduct the sandwich assay, reporter probe hybridization was performed as follows. The chip 12 was soaked in 1×STE buffer containing sonicated, denatured calf thymus DNA (100 µg/ml, Sigma, St. Louis, Mo.) at room temperature for five minutes. Afterwards, the buffer was drained and 15 µl of mixed solution (500 mM reporter probe in 1×STE buffer containing above mentioned calf thymus DNA) was put on the chip 12 and kept at room temperature for five minutes. The chip 12 was then washed five times with 15 µl of 1% SDS buffer made with 0.2×STE and soaked at room temperature in 5 ml of the same buffer for ten minutes. The chip was finally washed five times with 0.2×STE.

Figure 8A:
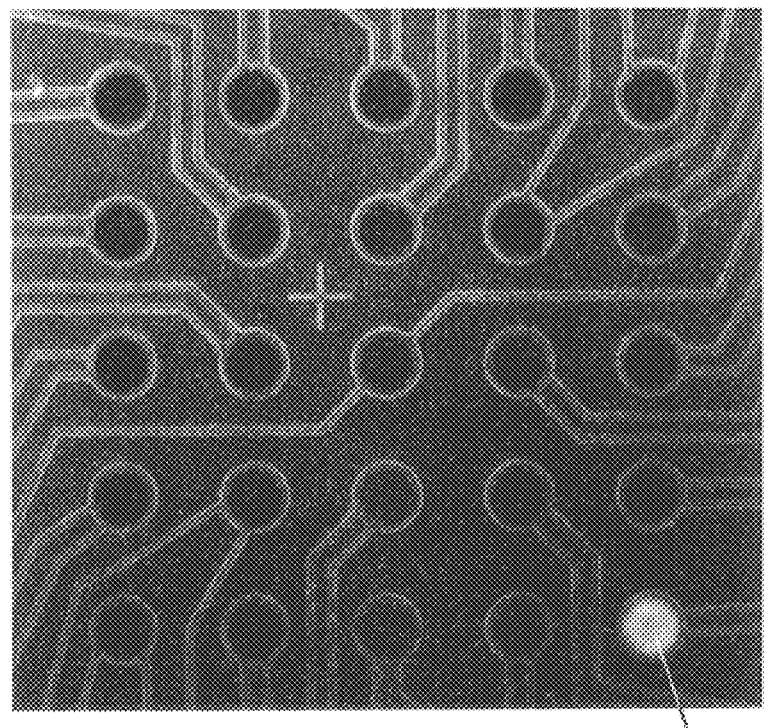
FIG. 8A shows a hybridization control to show specific capture by electronically-enhanced hybridization of plasmid DNA released from *E. coli*.
Figure 8B:
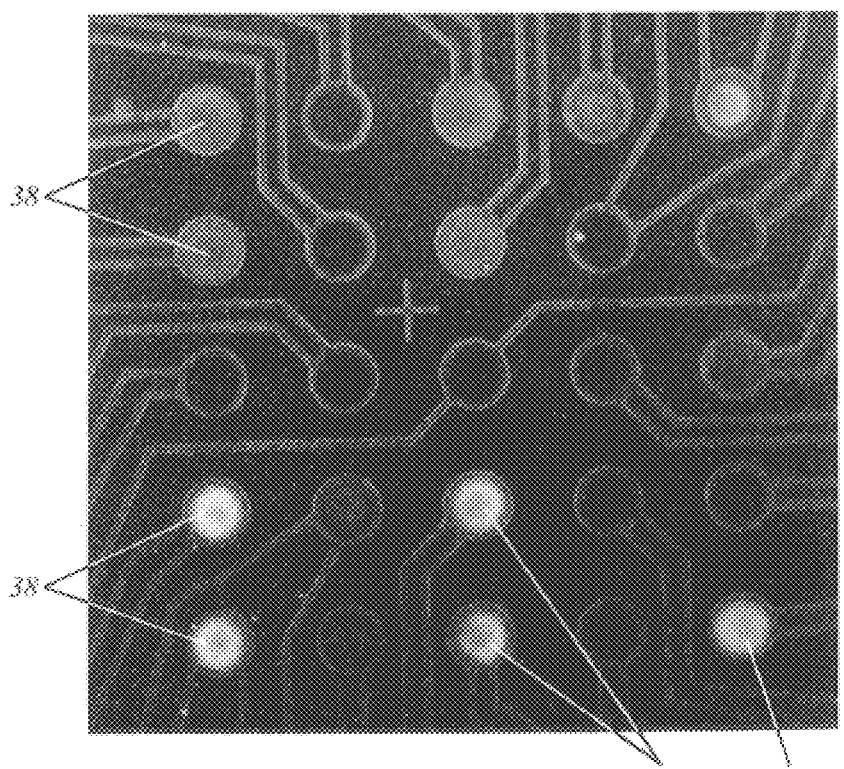
FIG. 8B shows the hybridization control of FIG. 8A and the results after a sandwich assay in which a sample of plasmid DNA from *E. coli* is electronically hybridized to additional probes.

FIG. 8A shows the hybridization control 37 for electronically-enhanced target capture of plasmid DNA released from E. coli, and FIG. 8B shows the results after a sandwich assay in which a sample of plasmid DNA 38 from E. coli is electronically hybridized to additional probes. As FIG. 8A shows, the immobilization chemistry of oligonucleotide probe worked as expected (i.e. the immobilized probe captured the oligonucleotide), and, as is shown in FIG. 8B, thermally treated plasmid DNA 38 obtained from electronic lysis can be used directly for hybridization-based assays with high reproducibility and without necessarily involving an enzymatic amplification process.

Then RNA hybridization was performed. The oligonucleotide capture probe 5'-XGAGTTGCAGACTCCAATCCG-GACTACGACG CACTTTA-3' specific for 16S RNA was incorporated with biotin at its 3' end. The probe was diluted in 50 mM L-histidine buffer to make a final concentration of 500 nM. The capture probe was immobilized on the test microlocations containing streptavidin with the underlying electrodes positively biased. The biasing was performed by maintaining the current on each electrode at 200 nA for one minute. Afterwards, the remaining probe solution was removed and the chip was washed with 50 mM L-histidine buffer. The immobilization of the probes for the controls (ATA5 and GAS probe) was accomplished using the same protocol described above.

To test the control, the synthesized RCA5 oligonucleotide target specific for capture probe ATA5 was electronically hybridized to both the immobilized ATA5 probe and the adjacent nonspecific GAS probe in parallel by keeping the current at each electrode at 450 nA for three minutes. The capture of the synthesized oligonucleotide target 5'-AATGGCGCATACAAAGAGAAGCGACCTCGCGA-GAGCAAGCGGACCTCATAAAGTGCGTCGTAGTCC-GGATTGGAGTATGCAACTCG-3' was performed as described above. To facilitate the hybridization of 16S RNA, a fraction of the proteinase K treated lysate was diluted three and five times respectively in the L-histidine buffer. The diluted lysate samples used above for plasmid DNA hybridization were also used here. When the capture processes were finished fresh Tris-phosphate buffer (20 mM Tris-base, 20 mM di-basic sodium phosphate, pH 9.0) was loaded to replace the L-histidine buffer to perform the electronic stringency wash. Simply performing electronic stringency washing in L-histidine buffer was insufficient in reducing non-specifically captured RNAs, but with the Tris-phosphate buffer the electronic stringency washing was very effective even with milder electric field conditions than those used with the L-histidine buffer. The washing was performed by applying 70 DC pulses to a row at a time, 750 nA per pad with 0.1 seconds on and 0.2 seconds off.

To conduct the sandwich assay the reporter probe hybridization was performed as follows. The chip was soaked in 1×STE buffer containing sonicated, denatured calf thymus DNA (100 $\mu$g/ml, Sigma, St. Louis, Mo.) at room temperature for five minutes. Afterwards, the buffer was drained and 15 $\mu$l of mixed solution (500 mM reporter probe in 1×STE buffer containing above mentioned calf thymus DNA) was put on the chip and kept at room temperature for five minutes. The chip was then washed five times with 15 $\mu$l of 1% SDS buffer made with 0.2×STE and soaked at room temperature in 5 ml of the same buffer for ten minutes. The chip was finally washed five times with 0.2×STE.

Figure 9A:
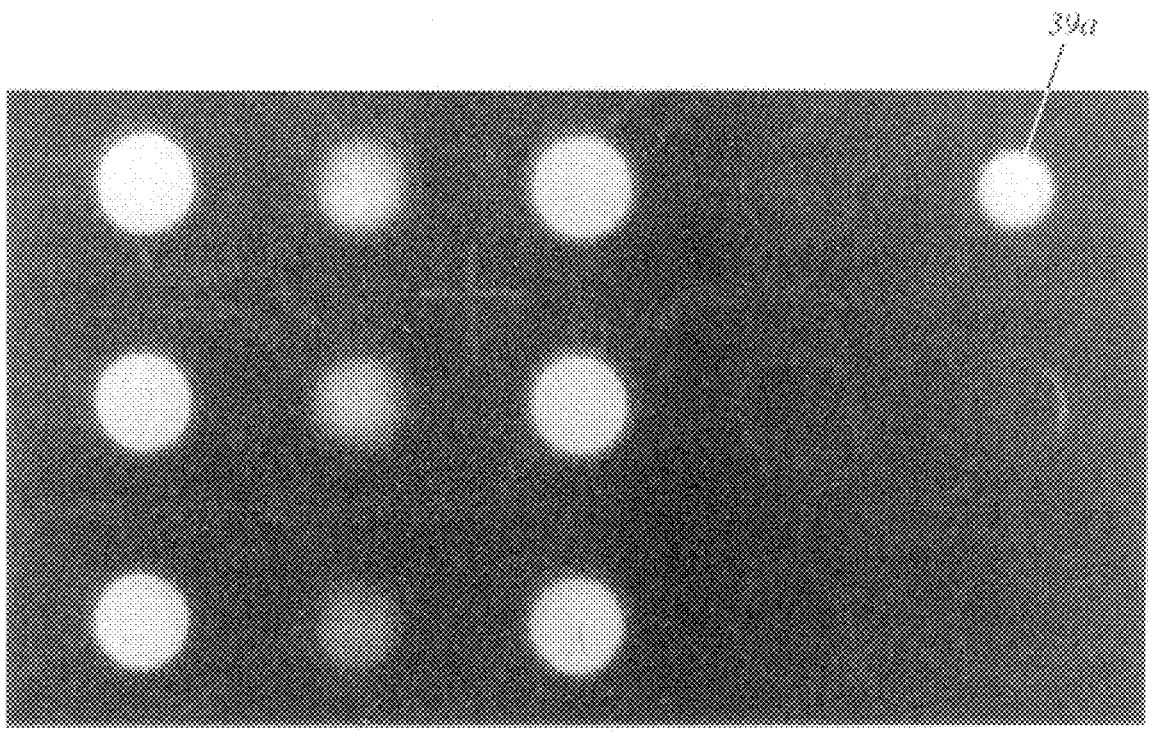
FIG. 9A shows a hybridization control to show specific capture by electronically-enhanced hybridization of ribosomal RNA released from *E. coli*.
Figure 9B:
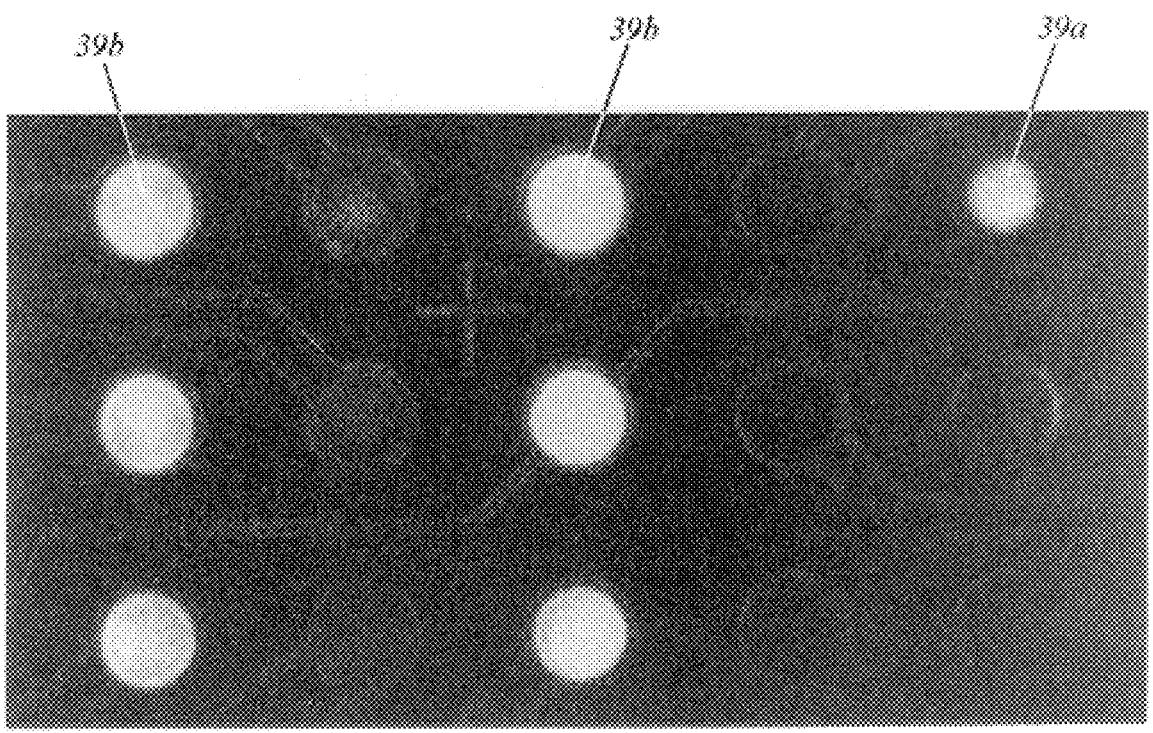
FIG. 9B shows the hybridization control of FIG. 9A and the results after a sandwich assay in which ribosomal 16S RNA from *E. coli* is electronically hybridized to additional probes.

FIG. 9A shows a hybridization control 39a for electronically-enhanced target capture of ribosomal RNA released from E. coli, and FIG. 9B shows the results after a sandwich assay in which ribosomal 16S RNA 39b from E. coli is electronically hybridized to additional probes. As FIG. 9A shows, the immobilization chemistry of oligonucleotide probe worked as expected (i.e. the immobilized probe captured the oligonucleotide), and, as is shown in FIG. 9B, thermally treated ribosomal RNAs 39b obtained from electronic lysis can be used directly for hybridization-based assays with high reproducibility and without necessarily involving an enzymatic amplification process.

The Cervical Carcinoma Test

As is mentioned above, the cartridge 10 was also used to separate and isolate cultured cervical carcinoma cells (HeLa cells) from peripheral blood cells in a mixture.

First a cell culture was prepared using well known techniques. The epithelial carcinoma cell line (HeLa) derived from a human cervical tumor was prepared by the core cell culture facility at the University of California at San Diego. The growth media (250 ml) was prepared by adding L-glutamine (2.5 ml, BRL Life Technologies) and fetal bovine serum (25 ml, Gemini Bio-Products) to RPMI 1640 (222.5 ml, BRL Life Technologies). To test the media for sterility, a portion of it (3 ml) was removed to a conical tube (15 ml) and the tube placed, with a loosened cap, in a 5% $CO_2$ incubator (National) at 37° C. for one week. The tube was checked for contamination every day for one week. Next, a frozen vial of cells (1.0 ml) was rapidly thawed by agitating in a 37° C. water bath. An equal volume of prewarmed media was then immediately added to the cells and the mixture transferred to a conical tube (15 ml). An additional portion of media (6 ml) was added to the cells to make a final volume of 8 ml. The cells were pelleted by centrifugation at 1100 rpm for two minutes. The supernatant was removed and the cell pellet resuspended in fresh media (10 ml). The cell suspension was incubated at 37° C. in the presence of 5% $CO_2$. The cells were harvested by trypsinizing the cells and then resuspending them in fresh media for immediate use. The cell count was $1\times10^6$/ml.

Then a cell mixture was prepared using well known techniques. The cell separation buffer comprised 0.0025× TBE (225 nM Tris, 225 nM boric acid, 5 nM EDTA, pH 8.2), 250 mM sucrose. The conductivity of the buffer was 10 $\mu$S/cm measured by an Accumet pH Meter 50 (Fisher Scientific, Pittsburgh, Pa.). The buffer conductivity for cell separation was chosen carefully to ensure that the HeLa cells will be subjected to positive dielectrophoresis and all normal blood cells negative dielectrophoresis. The cultured HeLa cell suspension (1 ml) was centrifuged at 325×g for four minutes and the supernatant removed. The cell pellet was washed in the cell separation buffer (1 ml) and pelleted using the same conditions described above. The HeLa cells were then resuspended in the cell separation buffer (1 ml). Fresh EDTA-anticoagulated human blood (1 ml) was spun at 400×g for five minutes and the supernatant removed. The packed cells (5 $\mu$l) were removed and added to the HeLa cell suspension (1 ml).

The dielectrophoresis system used in this test is as described above except that it also included a laser to aid in detection. The cartridge 10 was placed on an analytical probe station (Model 6000 Micromanipulator, Carson City, Nev.). Laser excitation was delivered by two He—Ne 594-nm lasers through optic fibers (6 mW output power; Research Electro-Optics, Boulder, Colo.) from an oblique angle. Image signals were collected by a cooled color charge-coupled device (CCD) camera (DEI-750T, Optronics International, Chelmsford, Mass.) through a 8×objective (numerical aperture 0.15) and a 630±25 nm band-pass filter. Image acquisition was achieved by means of a frame grabber (Scion, Frederick, Md.) and the IPLab 3.1.1 software on a Macintosh compatible StarMax 3000/200. Fluid pumping was accomplished with a peristaltic pump (Model RP-1, Rainin Instruments, Woburn, Mass.). Electrode signals were generated from a function/arbitrary waveform generator (Model HP33120A, Hewlett-Packard, Santa Clara, Calif.) and monitored by an oscilloscope (Model HP54600, Hewlett-Packard).

Figure 10A:
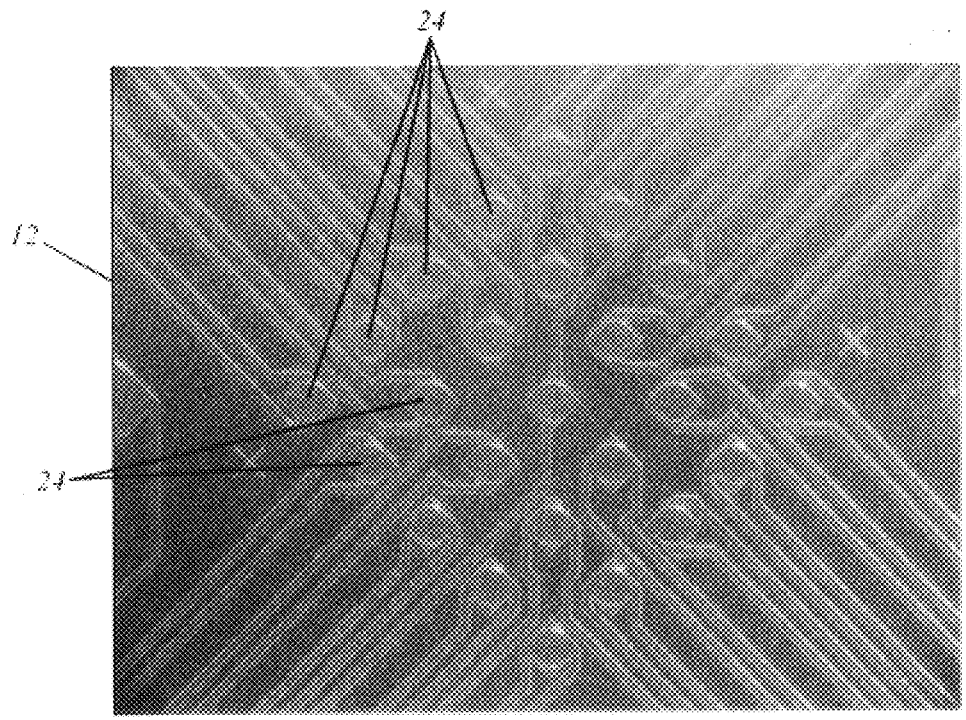
FIG. 10A is a view of the surface of a chip of the present invention after washing.
Figure 10B:
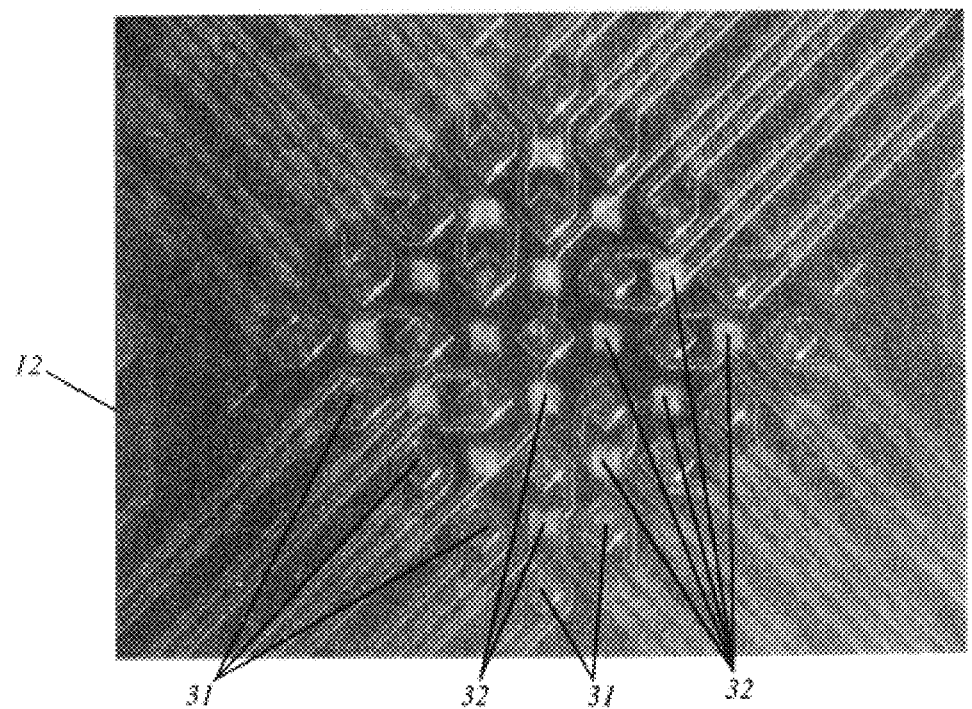
FIG. 10B shows a sample of HeLa cells retained on electrodes of the chip shown in FIG. 10A, and separated from human blood cells (both red and white blood cells) using the checkerboard style electronic addressing shown in FIGS. 3A and 3B.
Figure 10C:
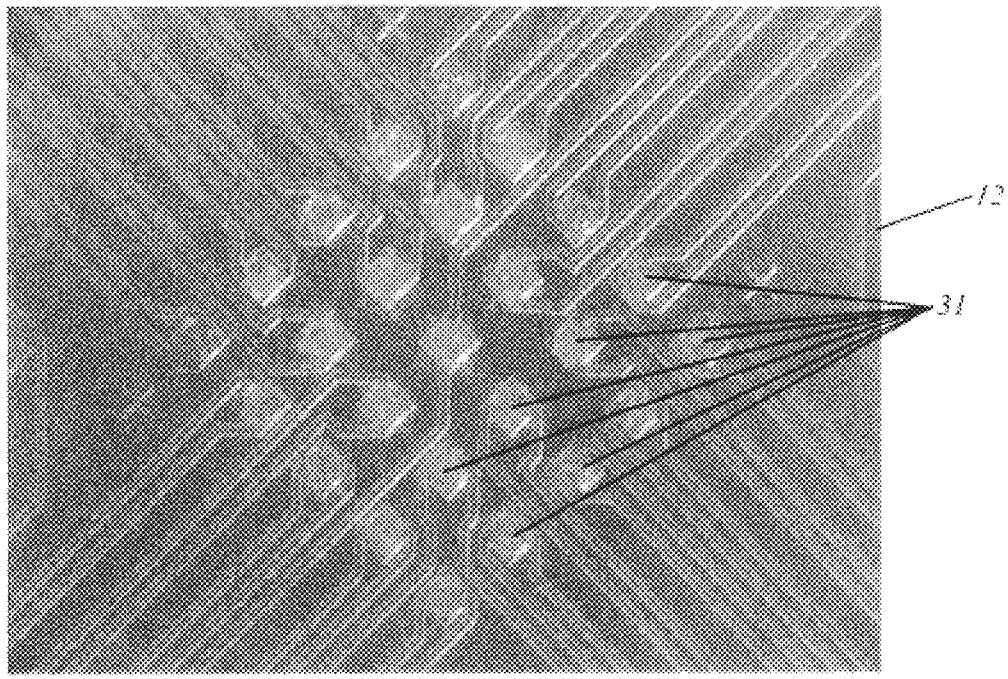
FIG. 10C shows the sample of HeLa cells of FIG. 10B after the human blood cells are washed away.

The HeLa cells were dielectrophoretically separated from the blood cells. The chip 12 was first washed by pumping separation buffer through the flow chamber (this also helped to wet the chip permeation layer and to remove any air bubbles in the chamber). FIG. 10A shows the surface of the chip 12 after washing. Next, the cell mixture was pumped into the flow chamber, and the pump was switched off. The entire array of electrodes 24 was addressed in a checkerboard format, described above, by applying a sinusoidal signal of 6 volts peak-to-peak at 30 KHz. As shown in FIG. 10B, the separation of HeLa cells 31 (collected at the electrodes 24 at the field maxima) from the peripheral human blood cells 32 (collected between the electrodes at the field minima 25) was complete in approximately three minutes. When the cell sample was nearly drained from the sample/buffer reservoir, separation buffer was pumped through the flow cell to wash the rest of the sample through while the AC signal was still on thereby allowing any additional HeLa cells carried into the flow chamber to be attracted to and retained by the electrodes 24, and to wash the peripheral human blood cells collected between the electrodes to be washed away. FIG. 10C shows the chip surface after this washing step.

To confirm that the cells on the electrodes were HeLa cells and not peripheral lymphocytes, buffy coat cells were prepared from the same blood, diluted with the same separation buffer and subjected to the same dielectrophoresis conditions. In this experiment, the lymphocytes were seen to move into the field minima between the electrodes and away from the electrodes confirming that the HeLa cells were on the electrodes.

Figure 10D:
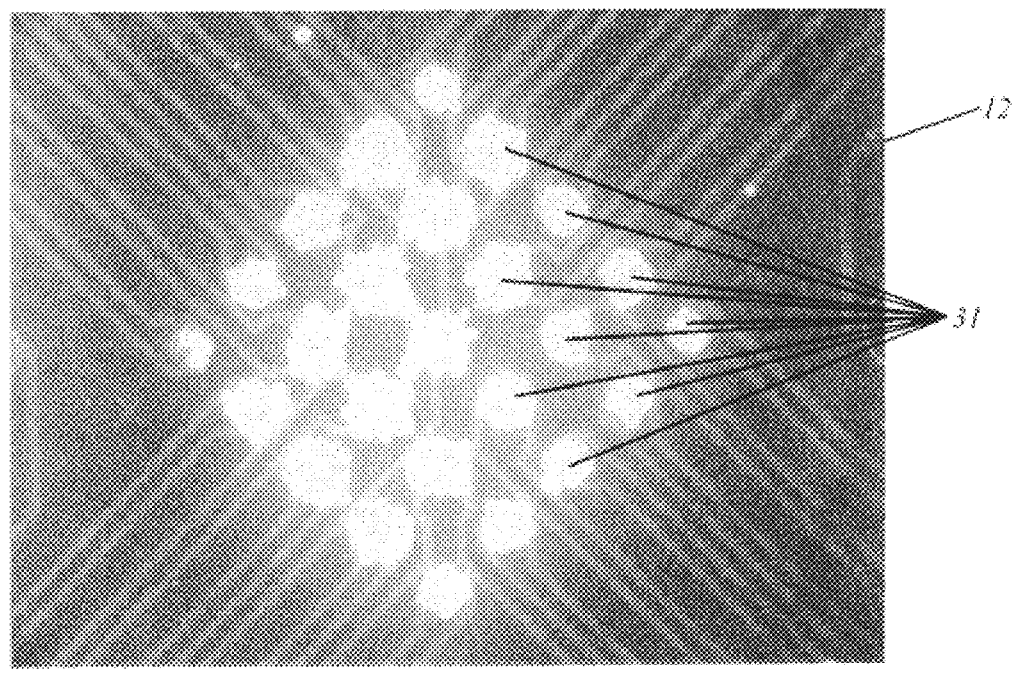
FIG. 10D shows the sample of HeLa cells of FIGS. 10B and 10C after staining.

The isolated HeLa cells were then stained through fluorescent staining as follows. The nucleic acid-binding fluorescent-dye, propidium iodide (2 $\mu$l, 1 mg/ml; Molecular Probes, Eugene, Oreg.) was added to the separation buffer (100 $\mu$l). When the cell isolation process was finished, the staining buffer was pumped into the flow cell. The staining process took about sixty seconds before the fluorescent image, which is shown in FIG. 10D, was captured. The resulting image enabled estimation of the diameter of the individual cells by comparing the size of the cells to the diameter of an electrode which is known to be 80 $\mu$m. The estimated size of the isolated cells on the electrodes varies from 17 to 34 $\mu$m which agrees with estimates obtained from viewing HeLa cells under an inverted microscope. In addition, the shape of these cells was more defined compared to lymphocytes which also confirms that they are HeLa cells. The isolated HeLa cells can be lysed and, if desired, subject to enzymatic reaction(s) as described above.

No convective movement of cells was observed during the dielectrophoretic separation process described above. As is mentioned above, this helps to minimize disturbing and washing off cells initially retained by the electrodes.

Additional Designs

Figure 11A:
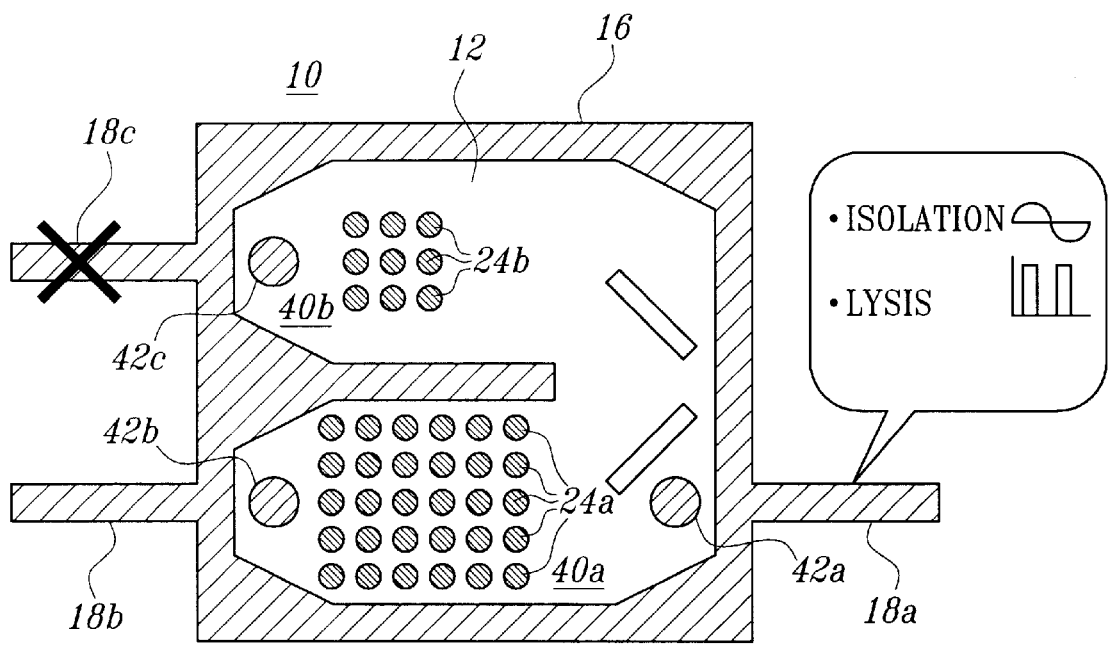
FIGS. 11A and 11B are cut-away schematic views of a self-contained flow chamber designed for performing cell separation, cell lysis, enzymatic deproteinization process of DNA/RNA, and/or DNA or RNA hybridization.
Figure 11B:
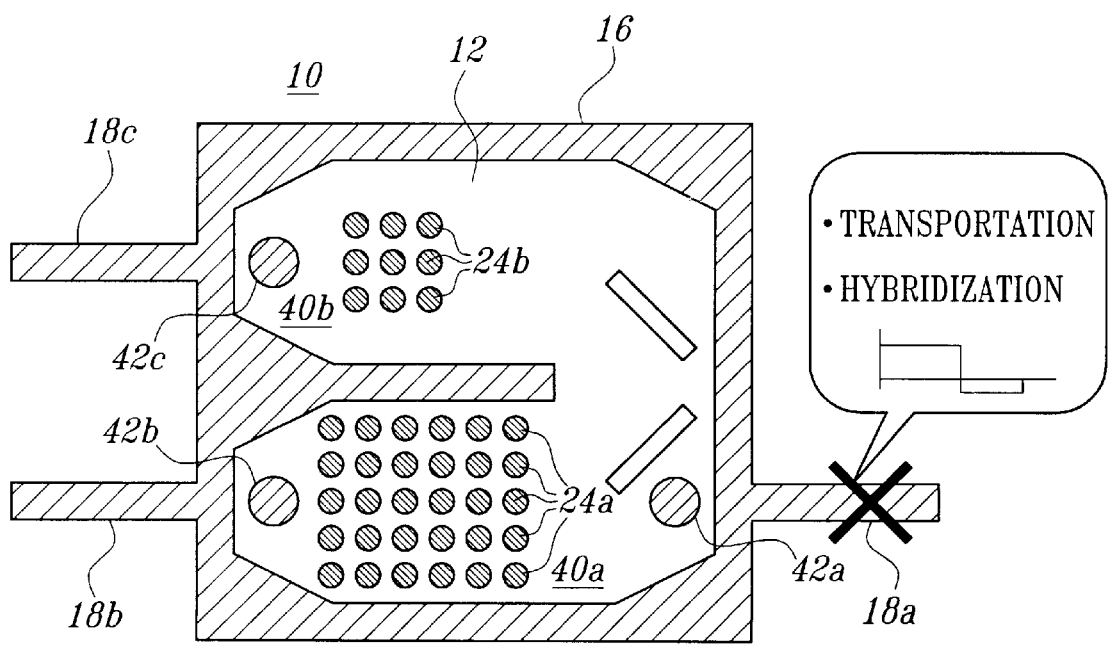

FIGS. 11A and 11B show cut-away schematic views of a design of a self-contained cartridge 10 for performing cell separation, cell lysis, enzymatic deproteinization process of DNA/RNA, and/or DNA or RNA hybridization. The cartridge 10 includes a U-shaped flow cell chamber 16 over a microchip 12. The microchip 12 includes an array of thirty electrodes 24a and four counterelectrodes 34a (not shown) in one arm 40a of the U-shaped chamber and an array of nine electrodes 24b in the other arm 40b of the U-shaped chamber. It should be noted that the number of electrodes used in the electrode arrays can differ from that shown here, and that the present specification shows an exemplary number of electrodes but is not limited to the same. Tubing 18a, 18b, and 18c is attached to the flow chamber 16 at vias 42a, 42b, and 42c which provide fluid communication into and out of the flow chamber 16.

One benefit of a U-shaped flow chamber such as that shown in FIGS. 11A and 11B is that different processes may be performed in essentially different chambers without having to physically remove and/or reintroduce the sample. For example, as is shown in FIG. 11A, tubing 18c is closed, and a sample is introduced through tubing 18a. Isolation and lysis of the desired cells takes place on electrodes 24a as is described above. Then, as is shown in FIG. 11B, tubing 18a is closed and tubing 18c is opened. The desired portion of the lysate is moved from arm 40a of the U-shaped chamber to arm 40b by manipulating flow through the flow cell and the electrical charge of the various electrodes in the cell 16. Then, for example, at electrodes 24b, the lysate is subject to hybridization or some other enzymatic reaction. This compartmentalization approach has the added benefit of avoiding interference from unwanted fragments in the lysate which did not fully wash away.

Figure 12A:
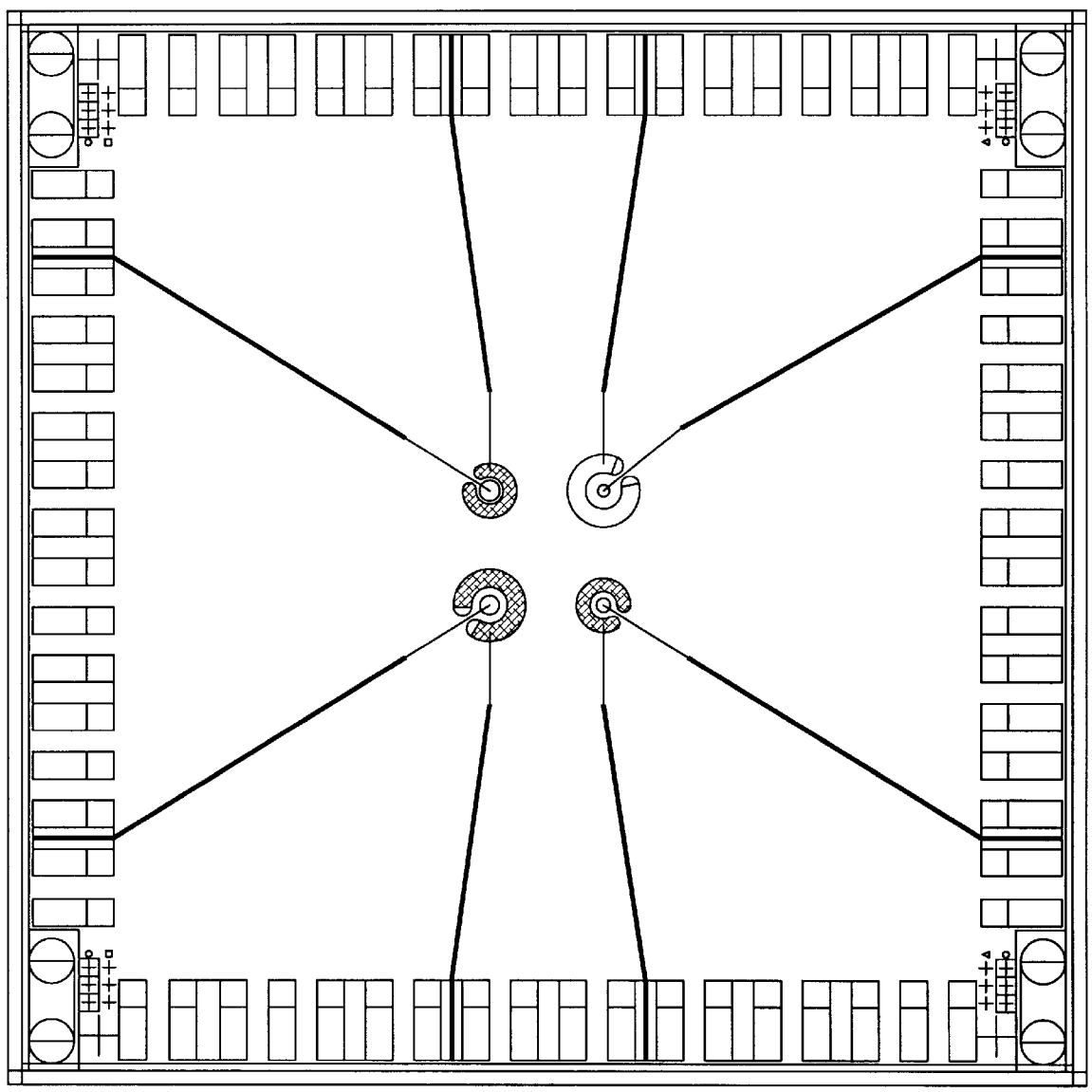
FIGS. 12A–D are, respectively, schematic views of four different microchip designs.

FIGS. 12A–D are schematic views of four different microchip designs which can be incorporated into the present invention. FIG. 12A shows a chip design for investigating optimal electrode dimensions for both dielectrophoresis and electronic lysis. It is believed that by using newly designed chips with a more expansive area covered by the microelectrodes, higher yield of desired cells can be achieved in less time.

Figure 12B:
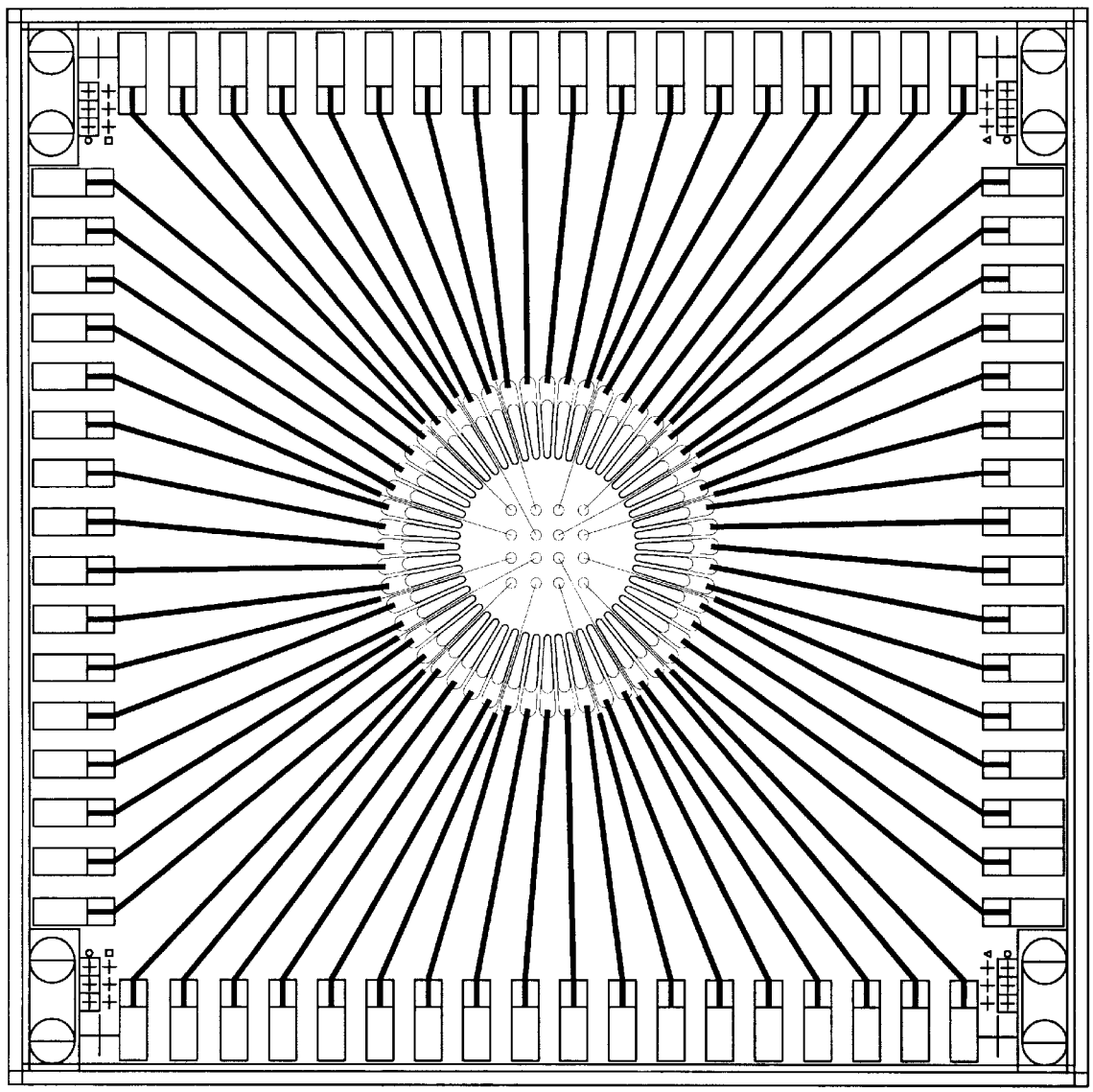

FIG. 12B shows a chip design that combines dielectrophoresis and travelling wave pumping features described above. The chip design shown in FIG. 12B provides a circular movement of the cell suspension introduced by applying a travelling wave (using a full face power supply) during the dielectrophoretic separation of cells (using the central microelectrode array).

Figure 12C:
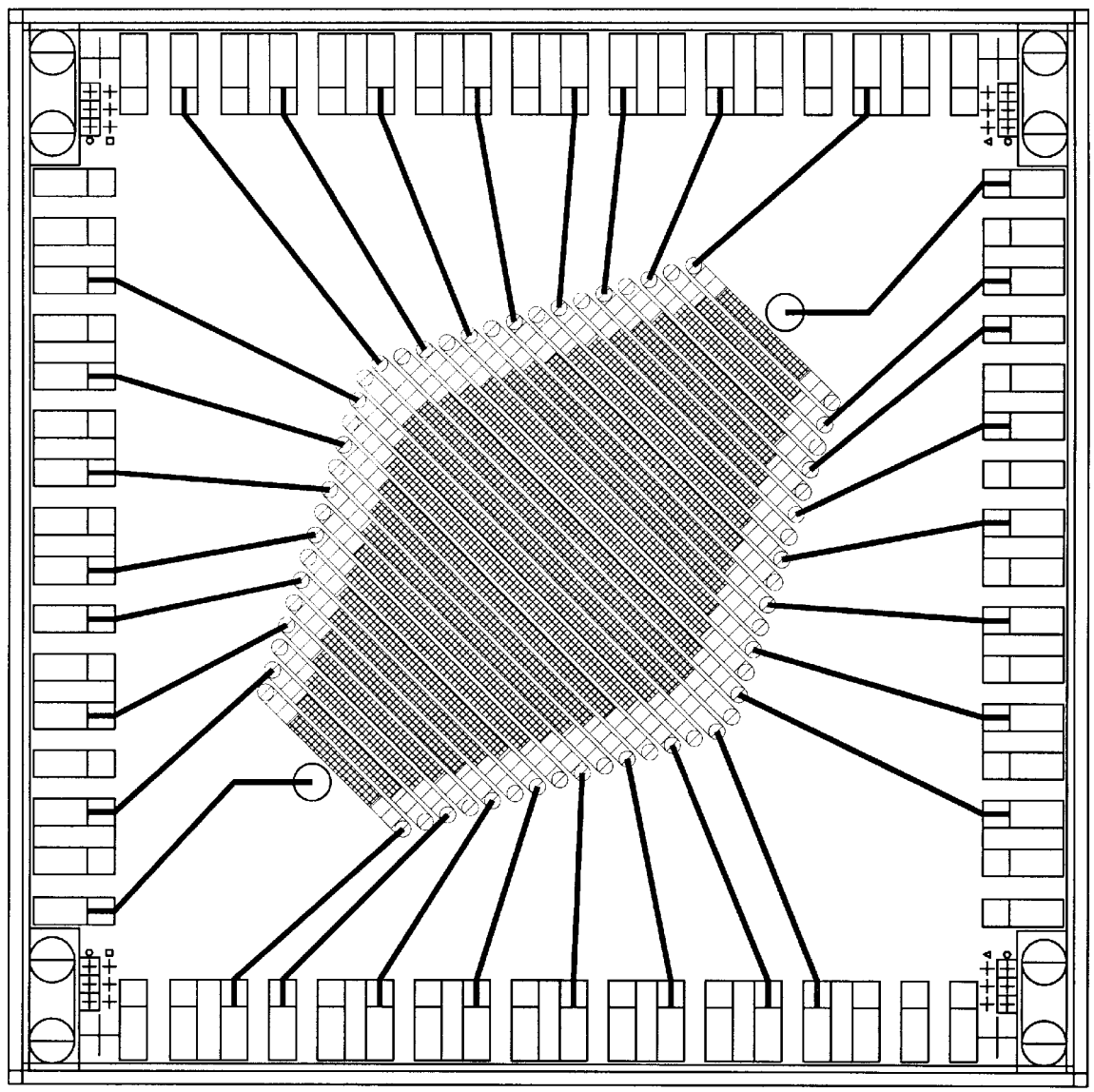
Figure 12D:
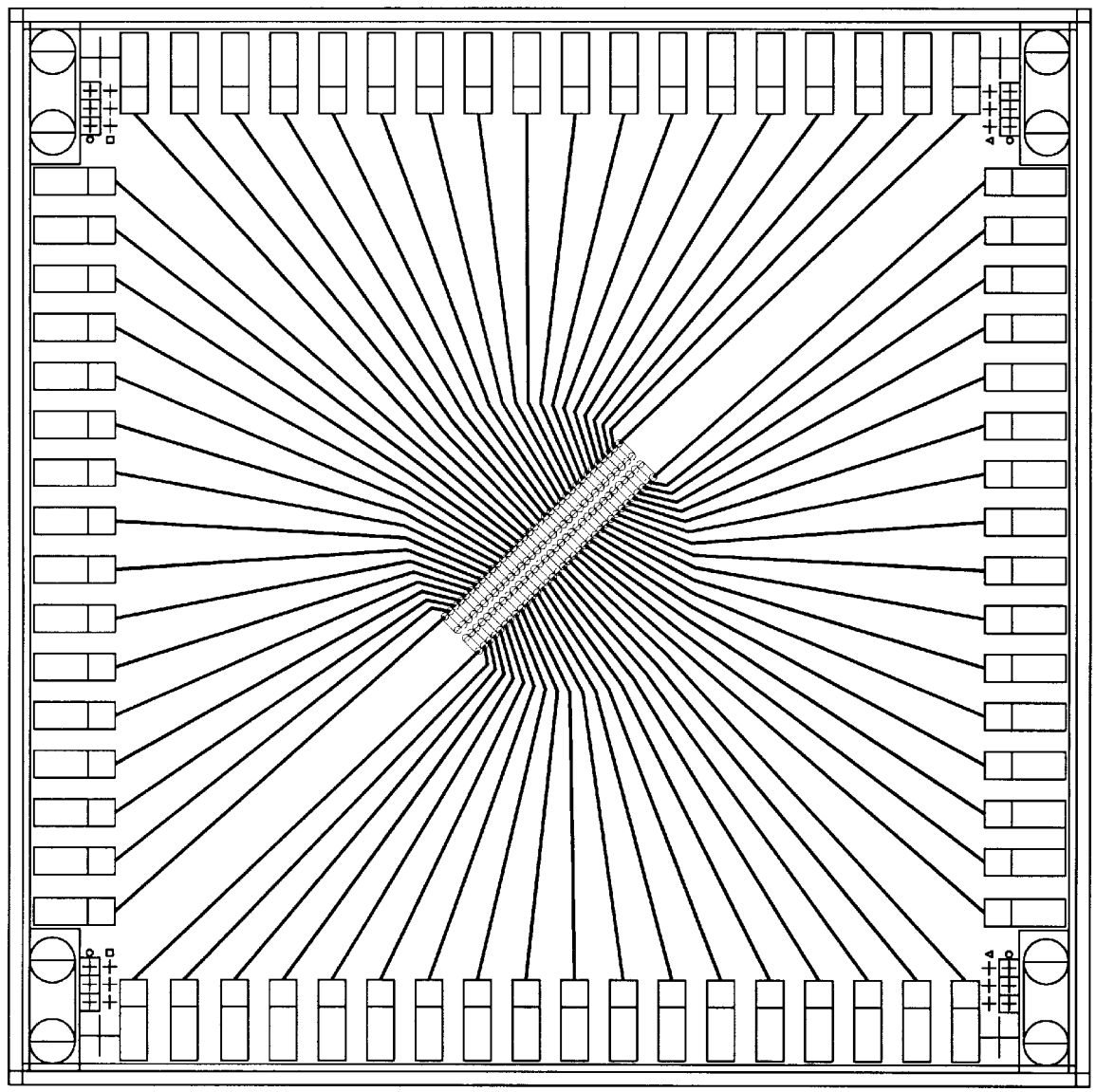

FIGS. 12C and 12D show chip designs for evaluating the use of travelling wave for separating and transporting cells.

While certain embodiments of the present invention have been shown and described in detail, it will be readily apparent to those skilled in the art, in light of these teachings, that certain changes and modifications may be thereto without departing from the spirit or scope of the appended claims.

What is claimed is:

1. An apparatus for at least one of separating, lysing, and enzymatically reacting biological samples, said apparatus comprising:
    a channel-less flow chamber having a partition for establishing more than one subchamber within the flow chamber, said flow chamber for accepting a biological sample, and
    a bioelectronic chip comprising a plurality of electrodes, wherein the electrodes are disposed in the flow chamber and are each capable of being biased, and wherein the chip and electrode surfaces in the flow chamber are coated with a permeation layer to prevent direct contact between said biological sample and said surfaces.

2. The apparatus of claim 1 wherein the plurality of electrodes comprises at least one array.

3. The apparatus of claim 2 wherein the plurality of electrodes comprises two arrays.

4. The apparatus of claim 1 wherein the flow chamber comprises a covered flow cell attached to the bioelectronic chip.

5. The apparatus of claim 1 wherein the permeation layer enables immobilization of a capture probe thereon.

6. The apparatus of claim 1 wherein the flow chamber has an approximate volume of about 10 microliters.

7. The apparatus of claim 1 wherein the electrodes are addressable in a checkerboard biasing format.

8. The apparatus of claim 1 wherein each electrode is addressable to enable biasing each electrode opposite from nearest neighboring electrodes.

9. The apparatus of claim 1 wherein the plurality of electrodes comprises groups of electrodes, and wherein each group is addressable to enable biasing each group of electrodes opposite from nearest neighboring groups of electrodes.

10. The apparatus of claim 1 further comprising at least one pair of counterelectrodes to enable electronic lysis through a series of electronic pulses between the electrodes and said counterelectrodes.

11. The apparatus of claim 10 comprising two pair of counterelectrodes.

12. The apparatus of claim 1 further comprising an immobilized capture probe on the permeation layer at the electrode surfaces in the flow chamber.

13. The apparatus of claim 12 wherein the capture probe comprises at least one of an antibody and ligand.

14. An apparatus for at least one of separating, lysing, and enzymatically reacting a biological sample, said apparatus comprising:

a channel-less flow chamber having a partition for establishing at least two subchambers within the flow chamber, said flow chamber for accepting a biological sample, a bioelectronic chip comprising a plurality of electrodes, wherein the electrodes are disposed in the flow chamber and are each capable of being biased, and wherein the flow chamber comprises a first subchamber and a second subchamber, and the plurality of electrodes comprise at least two electrode arrays, and wherein one electrode array is disposed in the first subchamber and one electrode array is disposed in the second subchamber.

15. The apparatus of claim 14 wherein the electrodes are addressable in a checkerboard biasing format.

16. The apparatus of claim 14 further comprising two pairs of counterelectrodes to enable electronic lysis through a series of electronic pulses between the electrodes and said counterelectrodes.

17. The apparatus of claim 14 wherein the flow chamber comprises a covered flow cell attached to the bioelectronic chip.

18. The apparatus of claim 17 wherein the chip and electrode surfaces in the flow chamber are coated with a permeation layer which enables immobilization of a capture probe thereon.

19. The apparatus of claim 18 wherein the capture probe comprises at least one of an antibody and ligand.

20. A method of manipulating biological samples comprising a mixture of desired cellular materials and undesired cellular materials, the manipulation being achieved in a dielectrophoretic system including a flow chamber having an array of electrodes, comprising the steps of:

introducing a cell mixture suspension into the flow chamber of the system;

subjecting the cell mixture suspension to an electric field by biasing the electrodes in a checkerboard format such that desired cells collect at the electrodes and undesired cells collect between the electrodes; and washing the undesired cells out of the flow chamber.

21. The method of claim 20 comprising the additional step of lysing the desired cells retained in the flow chamber of the system by subjecting the cells to a series of electronic pulses having alternating polarity.

22. The method of claim 21 comprising the additional step of subjecting the lysed material in the flow chamber of the system to an enzymatic reaction.

23. A method of manipulating biological samples comprising a mixture of desired cellular materials and undesired cellular materials, the manipulation being achieved in a dielectrophoretic system including a flow chamber having a first array of electrodes for separating and lysing, and a second array of electrodes which include oligonucleotide capture probes for hybridizing, comprising the steps of:

introducing a cell mixture suspension into the flow chamber of the system;

subjecting the cell mixture suspension to an electric field by biasing the first array of electrodes in a checkerboard format such that desired cells collect at the electrodes and undesired cells collect between the electrodes;

washing the undesired cells out of the flow chamber;

lysing the desired cells retained in the flow chamber of the system by subjecting the cells to a series of electronic pulses having alternating polarity;

subjecting the lysed material in the flow chamber of the system to an enzymatic reaction; and hybridizing the enzymatic reaction product by exposure to the second array of electrodes.

24. A method of manipulating biological samples comprising a mixture of desired cellular materials and undesired cellular materials, the manipulation being achieved in a dielectrophoretic system including a flow chamber having a first array of electrodes for separating and lysing, and a second array of electrodes which include oligonucleotide capture probes for hybridizing, comprising the steps of:

introducing a cell mixture suspension into the flow chamber of the system;

subjecting the cell mixture suspension to an electric field by biasing the first array of electrodes in a checkerboard format such that desired cells collect at the electrodes and undesired cells collect between the electrodes;

washing the undesired cells out of the flow chamber;

lysing the desired cells retained in the flow chamber of the system by subjecting the cells to a series of electronic pulses having alternating polarity;

subjecting the lysed material in the flow chamber of the system to an enzymatic reaction; and exposing the enzymatic reaction product to the second array of electrodes for ligand binding.

25. The method of claim 24 wherein the capture probes are immobilized antibodies.

\* \* \* \* \*

UNITED STATES PATENT AND TRADEMARK OFFICE
CERTIFICATE OF CORRECTION

PATENT NO. : 6,071,394
DATED : June 6, 2000
INVENTOR(S) : Jing Chen et al.

It is certified that error appears in the above-identified patent and that said Letters Patent is hereby corrected as shown below:

Column 8,
Line 6, please change "EPL" to -- BPL --.

Signed and Sealed this

Fifth Day of March, 2002

Attest:

JAMES E. ROGAN
Attesting Officer     Director of the United States Patent and Trademark Office